United States Patent [19]

Chung et al.

[11] Patent Number: 5,496,272

[45] Date of Patent: Mar. 5, 1996

[54] ARTIFICIAL INSEMINATION AND EMBRYO TRANSFER DEVICE

[75] Inventors: Byung H. Chung; Kil S. Chung; Hoon T. Lee, all of Seoul; Kyung K. Lee, Daejeon; Byeong H. Lee, Kyunggi-Do; Won C. Lee; Hwa J. Yoon, both of Seoul, all of Rep. of Korea

[73] Assignee: Kwahak International Co., Ltd., Kyunggi-Do, Rep. of Korea

[21] Appl. No.: 253,941

[22] Filed: Jun. 3, 1994

[30] Foreign Application Priority Data

| Jun. 4, 1993 | [KR] | Rep. of Korea | 93-10078 |
| Nov. 30, 1993 | [KR] | Rep. of Korea | 93-25806 |
| May 12, 1994 | [KR] | Rep. of Korea | 94-10334 |

[51] Int. Cl.$^6$ .................................................. A61M 31/00
[52] U.S. Cl. ............................ 604/55; 604/906; 606/191
[58] Field of Search ............................. 604/55, 187, 218, 604/192, 54, 220, 60, 61, 38, 135, 183, 264, 275, 207, 208, 906, 181, 73, 905, 283, 902, 265, 285, 217, 19, 15; 600/33, 34, 35; 128/761, 769, 778; 606/191

[56] References Cited

U.S. PATENT DOCUMENTS

| 586,776 | 7/1897 | Lewis | 606/191 |
| 1,767,785 | 6/1930 | Sushko | 606/191 X |
| 3,875,939 | 4/1975 | Bolduc et al. | 604/55 |
| 3,910,275 | 10/1975 | Babey et al. | 604/906 X |
| 3,938,504 | 2/1976 | Dickinson, III et al. | 606/191 X |
| 4,126,134 | 11/1978 | Bolduc et al. | 604/55 |
| 4,416,660 | 11/1983 | Dafoe | 604/55 |
| 4,432,753 | 2/1984 | Cassou et al. | |
| 4,642,094 | 2/1987 | North, Jr. et al. | 604/55 |
| 4,654,025 | 3/1987 | Cassou et al. | |
| 4,701,164 | 10/1987 | Cassou et al. | |
| 4,846,785 | 7/1989 | Cassou et al. | |
| 4,865,589 | 9/1989 | Simmet et al. | |
| 5,389,089 | 2/1995 | Bauer et al. | 604/271 |

FOREIGN PATENT DOCUMENTS

| 2647668 | 12/1990 | France | 604/34 |

Primary Examiner—C. Fred Rosenbaum
Assistant Examiner—V. Alexander
Attorney, Agent, or Firm—Finnegan, Henderson, Farabow, Garrett and Dunner

[57] ABSTRACT

An artificial insemination and embryo transfer device comprises an elongate hollow tube, and a hollow straw containing a reproductive organism therein and fitted in the elongate tube. A flexible tip is secured to an end of the elongate tube and engaged with the straw. The tip has a passage in communication with the straw and a conical portion adapted to smoothly pass it through a cervical canal of a female subject. A piston rod is slidably mounted in the elongate tube and constructed to enter into the straw so as to discharge the reproductive organism contained in the straw through the passage of the tip by its axial advancement. A locking element is disposed between the elongate tube and the piston rod for restraining a free axial movement of the piston rod within the elongate tube. A first enclosure is inserted around the elongate tube so as to protect the elongate tube against contamination from infectious materials in the cervical canal during the passing of the device through the cervical canal. A second enclosure surrounds the tip and the first enclosure for preventing them from being contaminated from infectious materials in a vaginal canal during the insertion of the device into the vaginal canal.

30 Claims, 21 Drawing Sheets

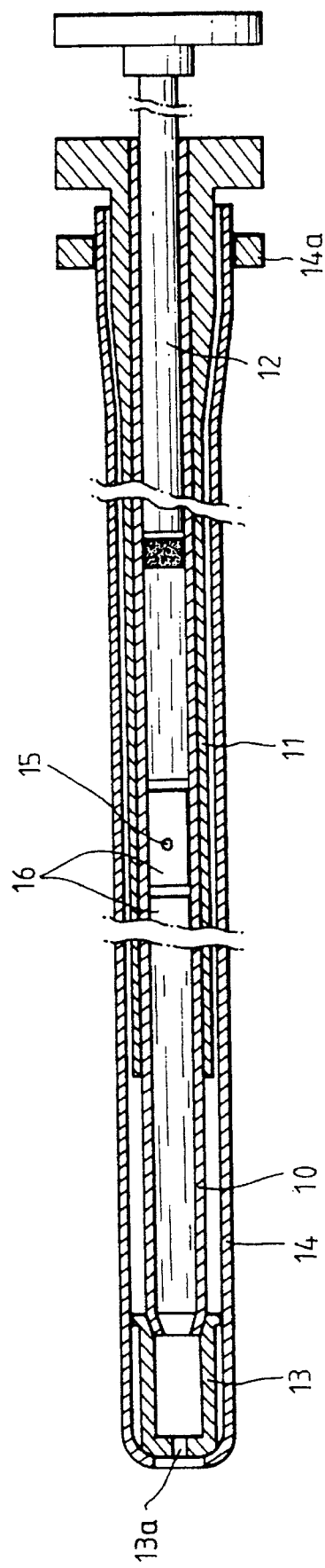
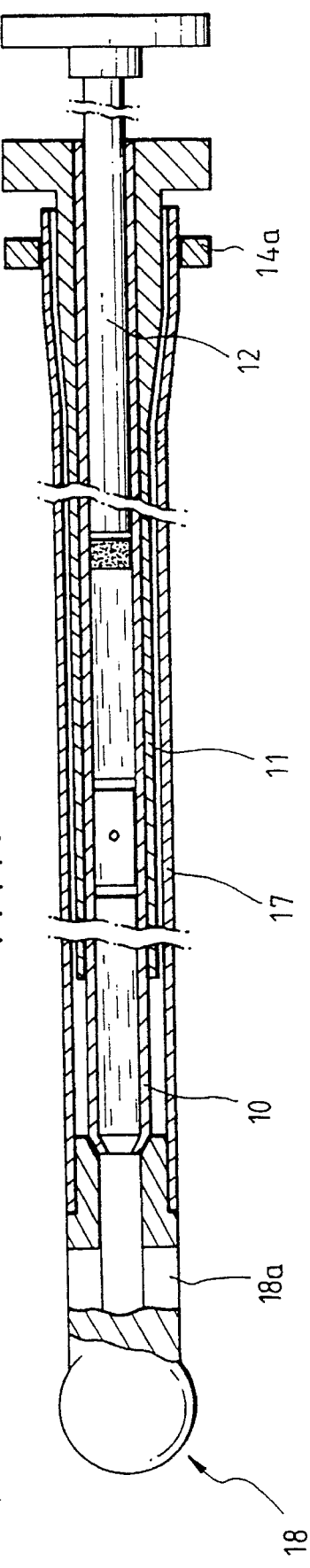
FIG. 3 (Prior Art)
FIG. 4 (Prior Art)

ARTIFICIAL INSEMINATION AND EMBRYO TRANSFER DEVICE

FIELD OF THE INVENTION

The present invention relates to an instrument for artificial insemination or embryo transfer; and, more particularly, to a device for transferring a reproductive organism of a mammal such as semen or embryo into a genital organ of a female to provide artificial insemination or embryo transplantation.

DESCRIPTION OF THE PRIOR ART

Various techniques have been proposed to provide artificial insemination or embryo implantation in the reproductive systems of humans and animals (e. g., a cow), which are schematically represented in FIGS. 1 and 2, showing a vagina 8, a cervical canal 2 and a uterine cavity 4. Usually, in order to enhance the rate of pregnancy by artificial insemination, sperms should be introduced to a rear zone of the cervical canal 2 or at a front zone 4a of the uterine cavity 4. In case of the embryo implantation, the embryo of the human should be deposited at a rear zone of the uterine cavity 4 and the embryo of the animal at a rearmost zone 6a of a uterine horn 6 so as to attain a better rate of conception. Particularly, care should be taken to avoid the contamination of the sperm or embryo during the artificial insemination or embryo implantation thereof.

Generally, the artificial insemination is performed by a non-surgical technique and the embryo transfer is done by a surgical or non-surgical technique depending on the structural characteristics of the reproductive system of the subject or the level of operator's transplanting skill. In the latter case, it is recognized that the rate of pregnancy obtained by the laparotomy technique is higher than that by the non-surgical operation due to the more accurate deposition of the embryo in an optimum zone of the uterine horn and the ability to better control the embryo contamination. However, there exist various deficiencies in the surgical embryo transfer: the complicated and highly time consuming procedure, relatively high cost, and likelihood of increasing damages to the object. Further, it is difficult to perform repeatedly the embryo implantation on the same subject by using the surgical technique. For these reasons, the operators are reluctant to employ the surgical embryo transplantation.

Accordingly, although the success rate of the non-surgical embryo transfer technique is somewhat lower, it is widely used to practice the embryo transfer on animals. In general, an instrument for performing the non-surgical artificial insemination or embryo transfer includes a hollow cylindrical catheter, a reproduction organism containing cartridge loaded in the catheter, and a piston rod movably inserted into the catheter for expelling the reproduction organism from the cartridge. In carrying out the artificial insemination or embryo transfer, the catheter is introduced into the vaginal and the cervical canals of the subject and then the sperm or embryo is discharged from the cartridge by the forward movement of the piston rod to thereby deposit it in the uterine cavity or the uterine horn. Particularly, in case of embryo implantation, it is preferred that the embryo be placed in the rearmost zone of the uterine horn so as to enhance the rate of fertilization.

On the other hand, according to the anatomy of an animal (e. g., a cow), as shown in FIG. 2A, the cervical canal 2 has an annular ring-shaped wall 3 consisting of a cartilaginous tissue, 5 which is in contraction; and is closed, under a normal condition, by the contraction of the annular ring-shaped wall to prevent virus in the vagina from penetrating into the uterine cavity. This structural operation renders it difficult for the catheter to progress into the uterine cavity through the cervical canal. Therefore, a mucous membrane of the cervical canal is often subjected to serious injuries due to the forcible insertion of the catheter into the cervical canal. In particular, a bleeding in the cervical wall may affect adversely the reproduction organism discharged from or contained in the cartridge, causing a reduced rate of pregnancy. Therefore, there is provided an artificial insemination or embryo transfer device for reducing lesions to the cervical wall of the animal, which includes a rounded tip of a rigid material mounted thereto, or is made of a slender type of configuration so as to facilitate the entry of the device into the cervical canal. However, this device involves the risk of piercing the cervical wall or the uterine horn wall because of the rigidity of the tip and the slenderness of the device.

Further, there have been proposed various artificial insemination or embryo transfer instruments for alleviating damage to the animals. For example, French Patent No. 7621438 discloses an instrument for artificial insemination which includes a hollow cylindrical body having a reservoir tube inserted thereinto, a piston rod movably fitted into the hollow body, and a protective sheath surrounding the hollow body and the reservoir. However, this instrument is not useful for embryo transfer as it cannot be introduced into the rearmost zone of the uterine horn under an aseptic condition without irritating the cervical wall and the interior membrane of the uterine cavity.

In U.S. Pat. No. 4,432,753, there is provided a multi-shot artificial insemination apparatus comprising a pistol-type holder, a reservoir tube fixed to the holder by a clamping ring and containing a semen therein, and a piston rod inserted into the holder for discharging the semen contained in the reservoir tube. This apparatus has a deficiency in that the semen may be liable to contamination during the artificial insemination due to the exposure of the reservoir tube in the vaginal cavity and the uterine canal.

U.S. Pat. No. 4,642,094 proposes a non-surgical embryo transfer device which consists of a plunger element having a plunger rod extending therethrough, a hollow stainless steel tip screwed into the plunger element, and an embryo containing straw inserted into the tip. In this transfer device, the uncovering of the tip may cause the embryo contamination and the tip of the rigid material may create damages to the genital organs.

Further disclosed in U.S. Pat. Nos. 4,654,025 and 4,865,589 are other types of apparatus for transferring reproduction organisms such as sperm or embryo into a uterine cavity of an animal. However, these apparatus have a common disadvantage in that their rigid tips may injure the cervical wall and the membrane of the uterus while performing an artificial insemination or embryo transplantation therein.

Also, U.S. Pat. No. 4,846,785 offers a surgical instrument with a metal needle, which can be used for artificial insemination or embryo transfer via a transperitoneal route. The above prior art suggests that an exemplary plastic needle of the instrument is intended for artificial insemination of goats and deer through the cervical route. This non-surgical technique is generally referred to a forceps or speculum method which involves dilating the vaginal cavity by using an expander and inserting the instrument into the cervical canal. In this instrument, since an end portion of the plastic needle is not supported, the needle may tend to bend when it is inserted into the cervical canal, making it difficult to introduce the needle into the uterine cavity. Therefore, this instrument cannot be employed to carry out artificial insemination or embryo transfer in animals having a cartilaginous tissue in the cervical canal such as a cow, a horse and the like. Further, the plastic needle of the instrument may be exposed to contaminants in the vagina, causing damages to the sperm or embryo.

A typical instrument for artificial insemination or embryo transfer is shown in FIG. 3. The instrument shown therein includes a hollow cylinder 11, a reproductive material storing straw 10 fitted into the hollow cylinder 11, a piston rod 12 movably inserted into the cylinder 11 for extracting the reproductive material from the straw 10, a solid tip 13 engaged with an end of the straw 10 and having a passage 13a, and a cylindrical sheath 14 enclosing the hollow cylinder 11 and the tip 13 and having an opening in communication with the passage 13a of the tip 13. The cylindrical sheath 14 is locked at the hollow cylinder 11 by means of a ring 14a inserted thereon.

According to the prior art instrument, in case of transferring the embryo, the instrument is inserted into the vaginal cavity and the cervical canal so as to reach a middle area of the uterine horn. Thereafter, the piston rod 12 is pushed in a forward direction to discharge the embryo 15 together with a liquid medium 16 stored in the straw 10 toward the uterine horn via the passage 13a of the tip 13. Otherwise, in the artificial insemination, the sperm is ejected from the straw 10 when the tip 13 is located at a front area of the uterine horn. However, this prior art device suffers from the defects that the contaminants and virus in the vaginal canal enter into the passage of the tip 13 through the opening of the sheath 14 during the introduction of the instrument into the uterine cavity to thereby contact with the sperm or embryo, decreasing the rate of conception; and the solid tip 13 may cause lesions and bleeding at the mucous membrane of the cervical canal and the uterine horn due to an excessive force exerted thereon and involve a risk of piercing the uterine horn and penetrating into an abdominal cavity.

FIG. 4 depicts another prior art instrument for transferring embryo (disclosed in U.S. Pat. No. 4,701,164), which is similar to that shown in FIG. 3 with the except of the structure of the tip. In this instrument, a plastic tip 18 is provided at a distal end of an external protective sheath 17. In addition, the plastic tip 18 is formed of a rounded shape and has two lateral orifices 18a provided therein. Similarly, the orifices 18a of the tip 18 are filled with the cervical and the uterine mucus when the instrument is introduced into the uterine cavity through the vaginal and the cervical canals, causing damages and contamination of the embryo. Further, since the protective sheath 17 is made of a semi-rigid plastic, the tip 18 can not reach a desired rearmost zone of the uterine horn, resulting in a poor rate in pregnancy.

A further prior art apparatus for transferring animal reproduction elements similar the one depicted in FIG. 4 except for the configuration of the tip is represented in FIG. 5. In this apparatus, a nozzle 20 made of a semi-rigid material is fitted into a rigid protective sheath 19 and has a linear passage 20a formed therein. However, there exist disadvantages in the above apparatus similar to those raised in the instrument of FIG. 4.

SUMMARY OF THE INVENTION

Accordingly, it is an object of the present invention to provide a device for artificial insemination and embryo transfer with a flexible tip which is capable of being smoothly introduced into a uterine cavity or a uterine horn without causing any damage to the genital organs.

It is another object of the present invention to provide an instrument for transferring a reproductive organism such as a sperm and an embryo, which is designed to prevent the contamination of the sperm and the embryo during the insertion of the instrument into a vagina and a cervix, enhancing the rate of pregnancy.

It is a further object of the present invention to provide an instrument for embryo transfer, which is capable of placing the embryo in a desired optimal zone of a uterine horn.

The above and other objects of the present invention are accomplished by providing a device for administering artificial insemination and/or embryo transfer, which comprises:

an elongate hollow tube having a flange provided at its distal end and an annular radial ridge inwardly formed at its inner wall;

a hollow straw adapted to contain a reproductive organism therein and fitted in said elongate tube and supported on the ridge of said elongate tube at its rear portion;

a flexible tip secured to a proximal end of said elongate tube and engaged with a front portion of said straw, said tip having a passage in communication with the straw and a conical front portion adapted to smoothly pass it through a cervical canal of a female subject;

a piston rod slidably mounted in said elongate tube and adapted to enter into said straw so as to discharge the reproductive organism contained in said straw through the passage of said tip by its axial advancement;

means disposed between said elongate tube and said piston rod for restraining a free axial movement of the piston rod within said elongate tube;

first means enclosing said elongate tube for protecting said elongate tube against contamination from infectious materials in the cervical canal during the passing of the device through the cervical canal; and second means surrounding said tip and said first contamination preventing means for protecting them against contamination from infectious materials in a vaginal canal during the insertion of the device into the vaginal canal.

In another embodiment of the present inventions there is provided a device for administering artificial insemination and/or embryo transfer, which comprises:

an elongate hollow tube having a flange provided at its distal end and an annular radial ridge inwardly formed at its inner wall;

a hollow straw adapted to contain a reproductive organism therein and fitted in said elongate tube and supported on the ridge of said elongate tube at its rear portion;

a flexible tip secured to a proximal end of said elongate tube and engaged with a front portion of said straw, said tip having a conical front portion adapted to smoothly pass it through a cervical canal of a female subject, a tapered middle portion integrally formed with the conical portion, a main body portion integrally formed with the middle portion, and a passage provided therein for communicating with the straw;

a piston rod slidably mounted in said elongate tube and adapted to enter into said straw so as to discharge the reproductive organism contained in said straw through the passage of said tip by its axial advancement;

means disposed between said elongate tube and said piston rod for restraining a free axial movement of the piston rod within said elongate tube;

a support sleeve housing said elongate tube and said main body portion of said tip and in contact with the tapered middle portion at its front end for supporting the tip so as to permit the deformation of the tip, said support sleeve having a flange provided at its rear end, the outer diameter of said support sleeve being smaller than the largest diameter of said tip;

first means enclosing said support sleeve and said tip for protecting them against contamination from infectious materials in the cervical canal during the, passing of the device through the cervical canal; and second means surrounding said first contamination preventing means for protecting said first means against contamination from infectious materials in a vaginal canal during the insertion of the device into the vaginal canal.

In accordance with a further embodiment of the present invention, there is provided a device for administering artificial insemination and/or embryo transfer, which comprises:

an elongate hollow tube having a flange provided at its distal end and an annular radial ridge inwardly formed at its inner wall;

a hollow straw adapted to contain a reproductive organism therein and fitted in said elongate tube and supported on the ridge of said elongate tube at its rear portion;

a flexible tip secured to a proximal end of said elongate tube and engaged with a front portion of said straw, said tip having a conical front portion adapted to smoothly pass it through a cervical canal of a female subject, a tapered middle portion integrally formed with the conical portion, a main body portion integrally formed with the middle portion, and a passage provided therein for communicating with the straw;

a piston rod slidably mounted in said elongate tube and adapted to enter into said straw so as to discharge the reproductive organism contained in said straw through the passage of said tip by its axial advancement;

means disposed between said elongate tube and said piston rod for restraining a free axial movement of the piston rod within said elongate tube;

a support sleeve housing said elongate tube and said main body portion of said tip and in contact with the tapered middle portion at its front end for supporting the tip so as to permit the deformation of the tip, said support sleeve having a flange provided at its rear end, the outer diameter of said support sleeve being smaller than the largest diameter of said tip;

means enclosing said support sleeve and said tip for protecting them against contamination from infectious materials in a vaginal canal and the cervical canal during the introduction of the device into a uterine cavity, said contamination preventing means including a tubular member inserted around said tip and said support sleeve and having a rectangular flange provided at its distal end, a rupturable thin film cap attached to a proximal end of the tubular member, and a stretchable thin capsule secured to the proximal end of the tubular member and disposed inside the film cap for enwrapping the tip, said thin capsule having a breakable portion integrally formed therewith and arranged in a substantially coaxial relationship with the passage of the tip; and means provided at the flange of said support sleeve for holding the flange of said elongate tube and the rectangular flange of said tubular member.

BRIEF DESCRIPTION OF THE DRAWINGS

The above and other objects, features and advantages of the present invention will become apparent from the following detailed description of preferred embodiments given in conjunction with the accompanying drawings, wherein like numerals refer to like parts in different views:

FIGS. 3 to 5 represent various prior art instruments for artificial insemination or embryo transfer;

DETAILED DESCRIPTION OF THE PREFERRED EMBODIMENTS

Figure 1:
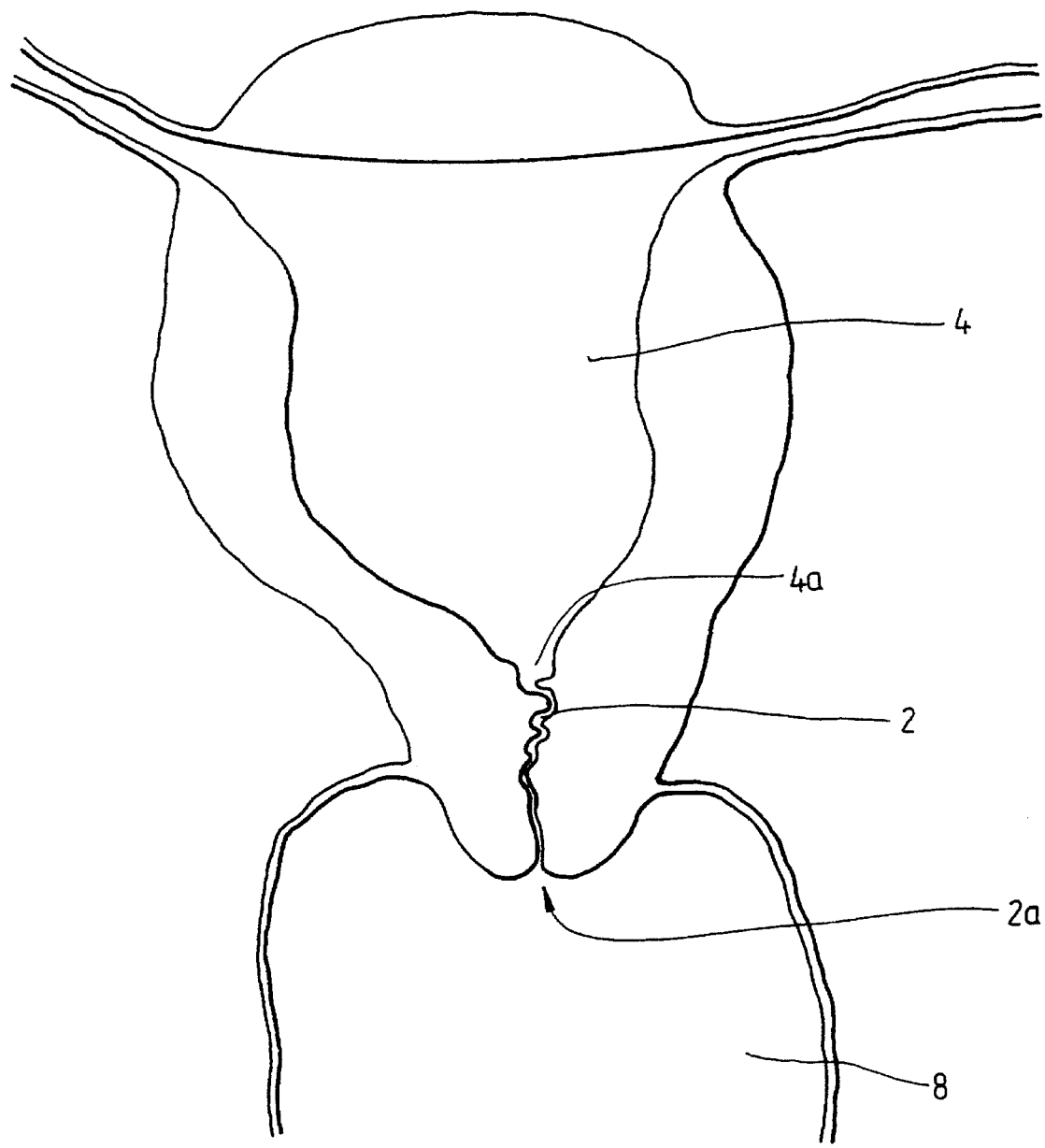
FIG. 1 shows a reproductive system of a human.
Figure 2:
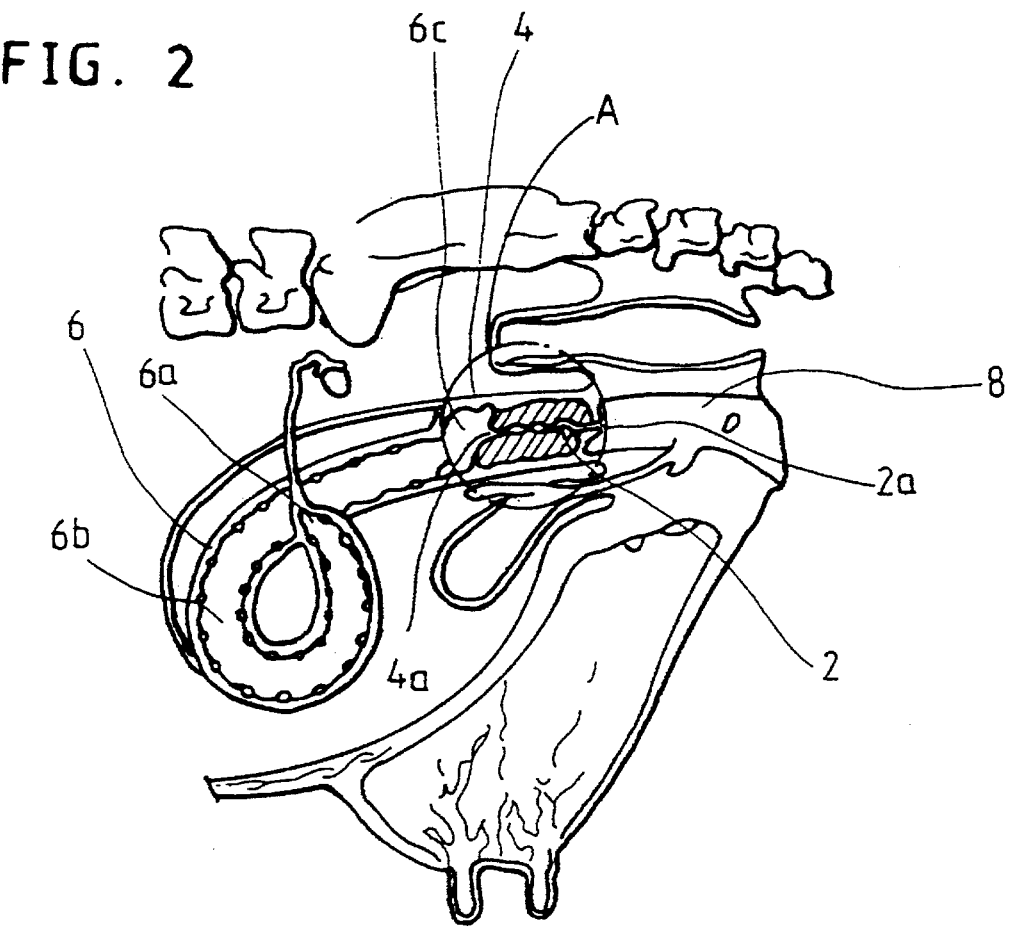
FIG. 2 depicts a reproductive system of a cow.
Figure 2A:
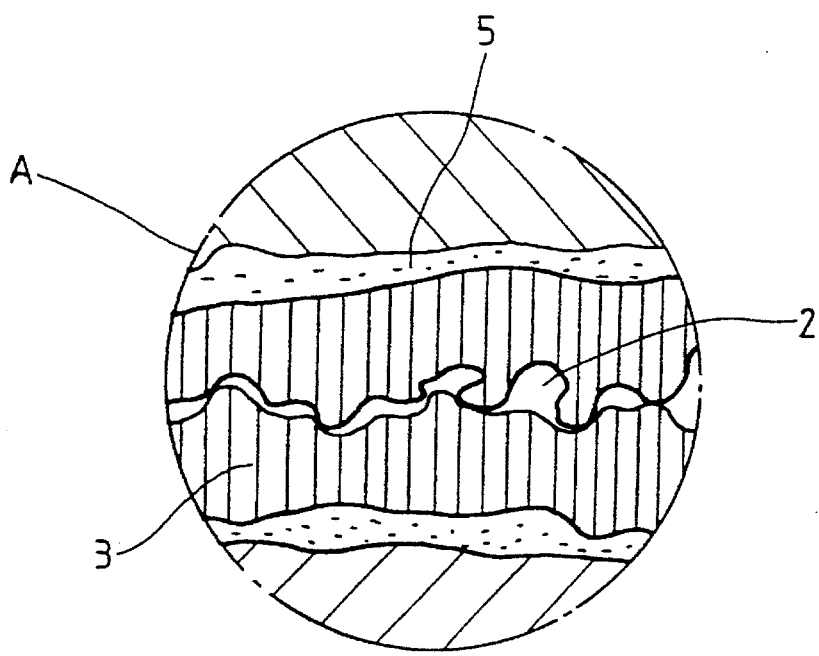
FIG. 2A is an enlarged partial view of a portion A of the reproductive system depicted in FIG. 2.
Figure 5:
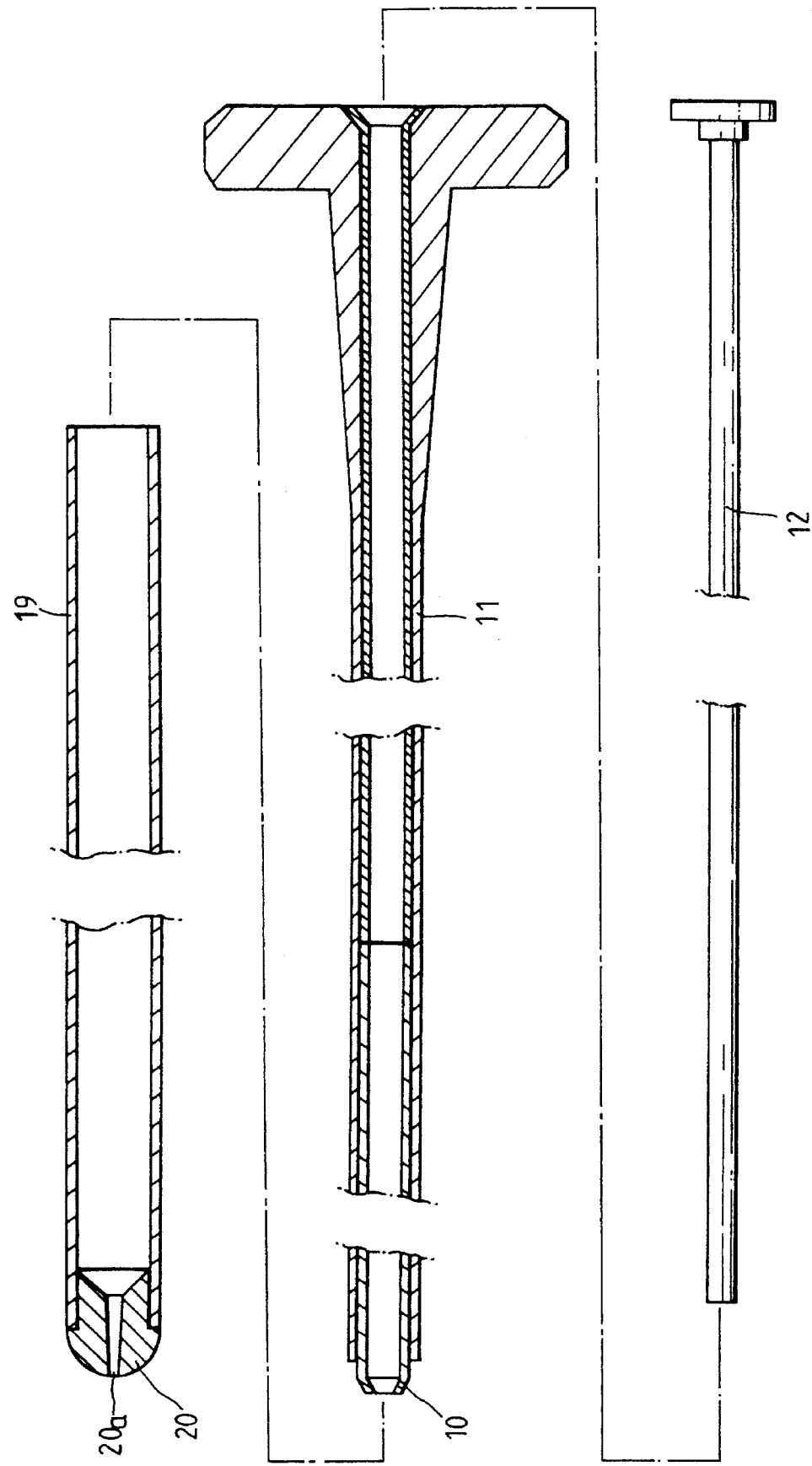
Figure 6:
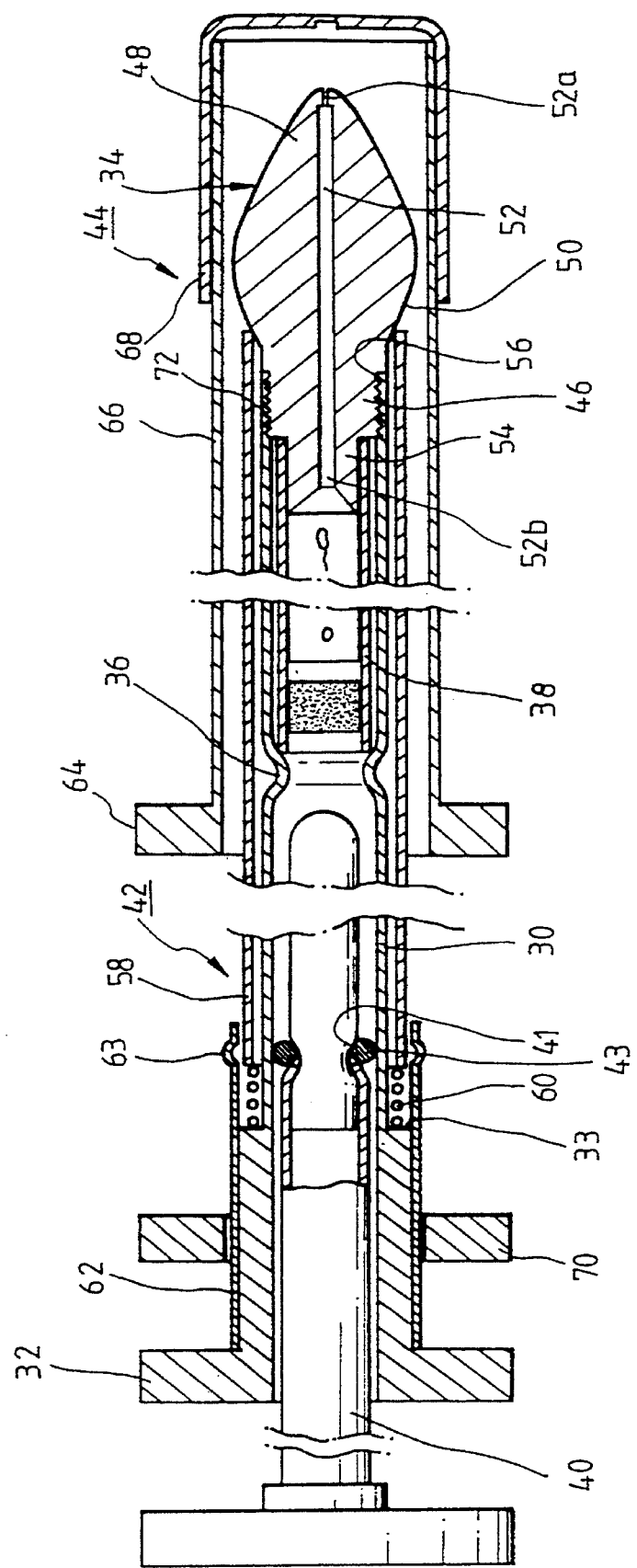
FIG. 6 is an enlarged sectional view of an artificial insemination and embryo transfer device in accordance with a preferred embodiment of the present invention.

Referring now to FIG. 6, there is shown an artificial insemination and embryo transfer device for humans and animals in accordance with a preferred embodiment of the present invention. The artificial insemination and embryo transfer device is provided with an elongate hollow tube 30 which includes a flange 32 formed at a distal end thereof and an annular radial ridge 36 inwardly formed at its inner wall. A flexible tip 34 is threadedly engaged with a proximal end of the elongate hollow tube 30. In addition, fitted in the elongate hollow tube 30 is a hollow straw 38 adapted to contain a reproductive material such as sperm or embryo therein, a rear portion of which is supported on the ridge 36 of the elongate tube 30 and a front portion of which is fitted to the deformable tip 34. A piston rod 40 is slidably mounted in the elongate tube 30 so that it enters into the straw 38 by its axial forward movement, thereby discharging the reproductive material stored in the straw 38. Mounted between the elongate tube 30 and the piston rod 40 is an O-ring 43 for restraining a free axial movement of the piston rod 40 in the elongate tube 30, which is held in an annular groove 41 of the piston rod 40. Further, the artificial insemination and embryo transfer instrument includes a first means 42 enclosing the elongate tube 30 for preventing the tube 30 from being contaminated by viruses and impurities in the cervix of a female subject during the passing of the device through the cervical canal and a second means 44 surrounding the tip 34 and the first contamination preventing means 42 for preventing them from being contaminated from germs and impurities in the vagina during artificial insemination or embryo implantation as will be described in detail hereinbelow. The ridge 36 of the elongate tube 30 serves to retain the straw 38 in place within the tube 30 and to guide an axial movement of the piston rod 40 with accuracy.

The elongate tube 30 and the piston rod 40 are generally made of a rigid material. The tip 34 is preferably made of a flexible material such as a non-toxic polymer and rubber (e.g., silicone rubber) so as to deform it in a shape compatible with the cervical canal and a uterine horn and to smoothly pass therethrough. As a result, this enables the tip 34 to easily bend and advance along meanders of the cervical canal and the uterine horn without causing any damage to the cervical wall and the uterine horn wall. Therefore, in accordance with the present invention, in case of the artificial insemination or embryo transfer of a heifer cow, for instance, an expander is not required to dilate the cervical canal for the purpose of passing the tip 34 through the cervical canal. The deformable tip 34 consists of a main body 46, a tapered middle portion 50 integrally formed with the main body 46 and in contact with the first contamination preventing means 42, a conical front portion 48 integrally formed with the middle portion 50 and adapted to smoothly pass it through the cervical canal, and a passage 52 in communication with the straw 38 for discharging the reproductive organism and a medium liquid contained in the straw therethrough. The passage 52 of the tip 34, in terms of its diameter, may be varied depending on the application of the instrument. In particular, the diameter of the passage 52 of the tip 34 is substantially smaller than that of the straw 38 so as to minimize the remaining amount of the reproductive material and the medium in the passage of the tip during the artificial insemination or embryo transplantation. Further, in case that the instrument is used for artificial insemination without the second contamination preventing means, preferably, an outlet port 52a of the passage 52 may be smaller at its diameter than an inlet port 52b of the tip 34, thereby minimizing the infiltration of mucus and virus from the cervical canal into the passage 52 of the tip 34 when the tip 34 passes through the cervical canal. This results in the prevention of the contamination of the sperm or embryo.

Figure 12:
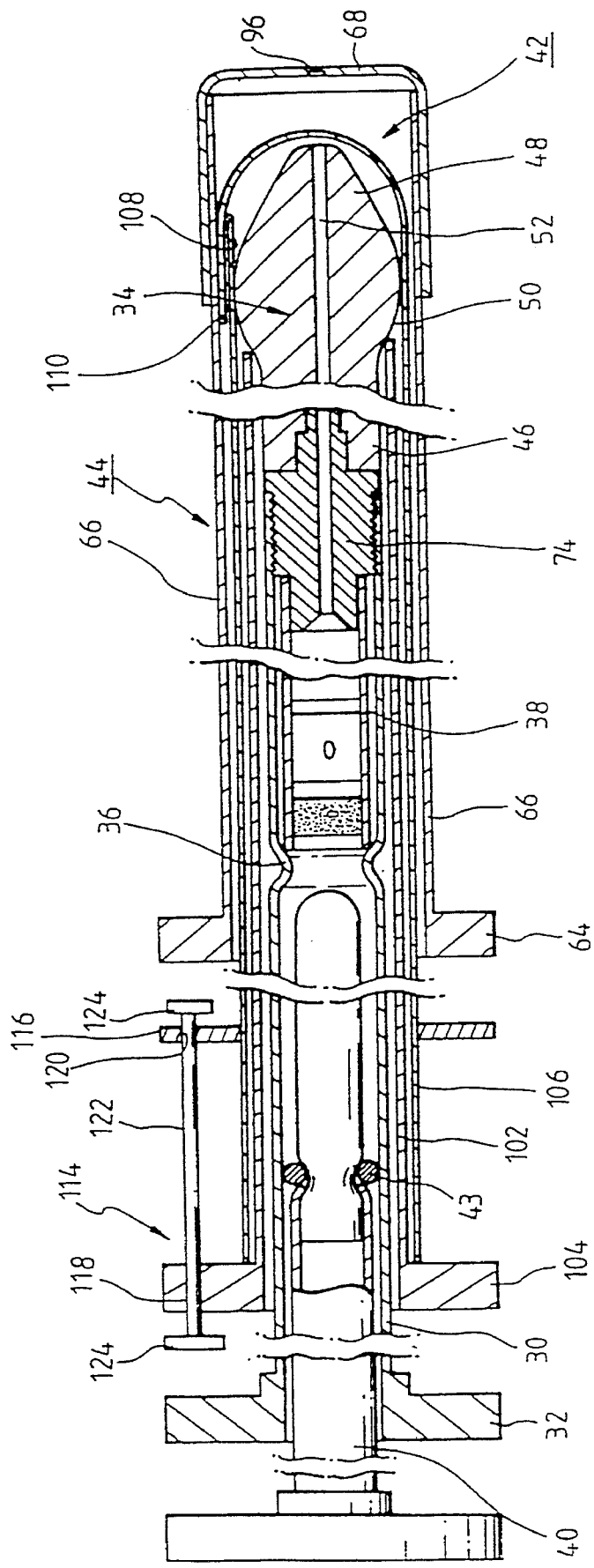
FIG. 12 is an enlarged sectional view of another embodiment of an artificial insemination and embryo transfer device in accordance with the present invention.
Figure 16:
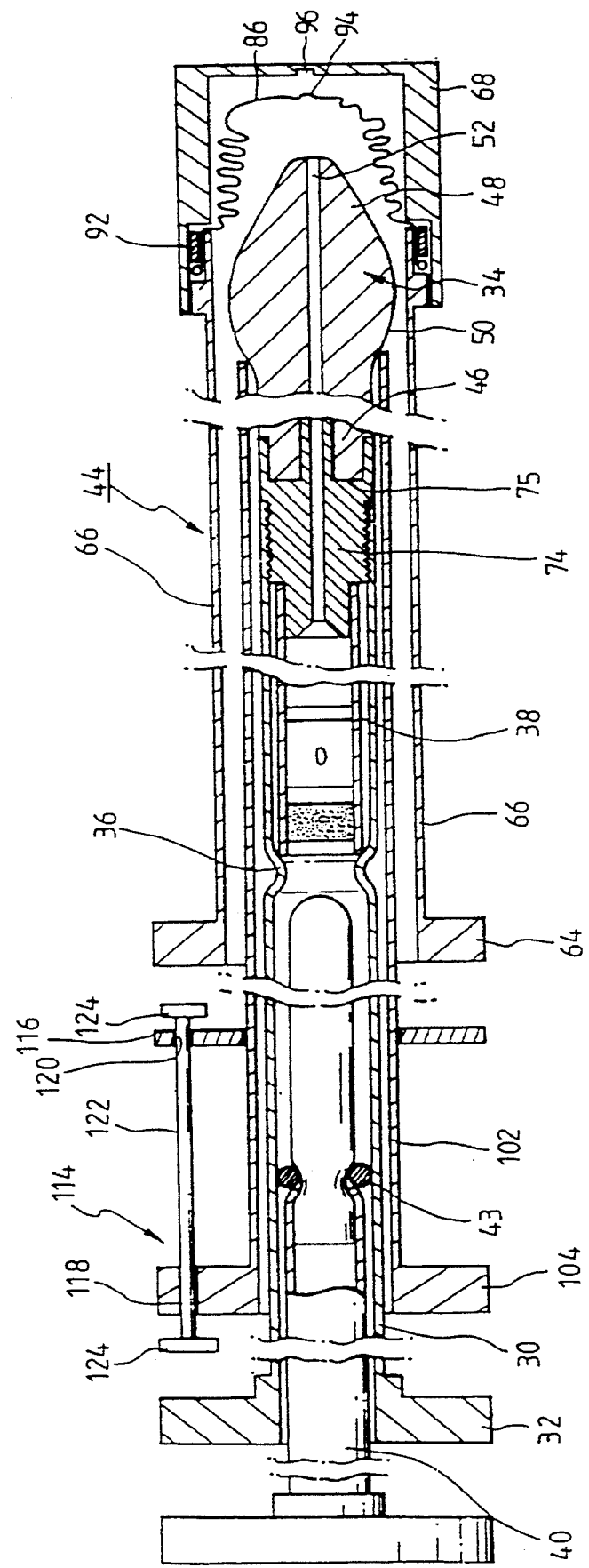
FIG. 16 is an enlarged sectional view of a further modified embodiment of an artificial insemination and embryo transfer device in accordance with the present invention.
Figure 24:
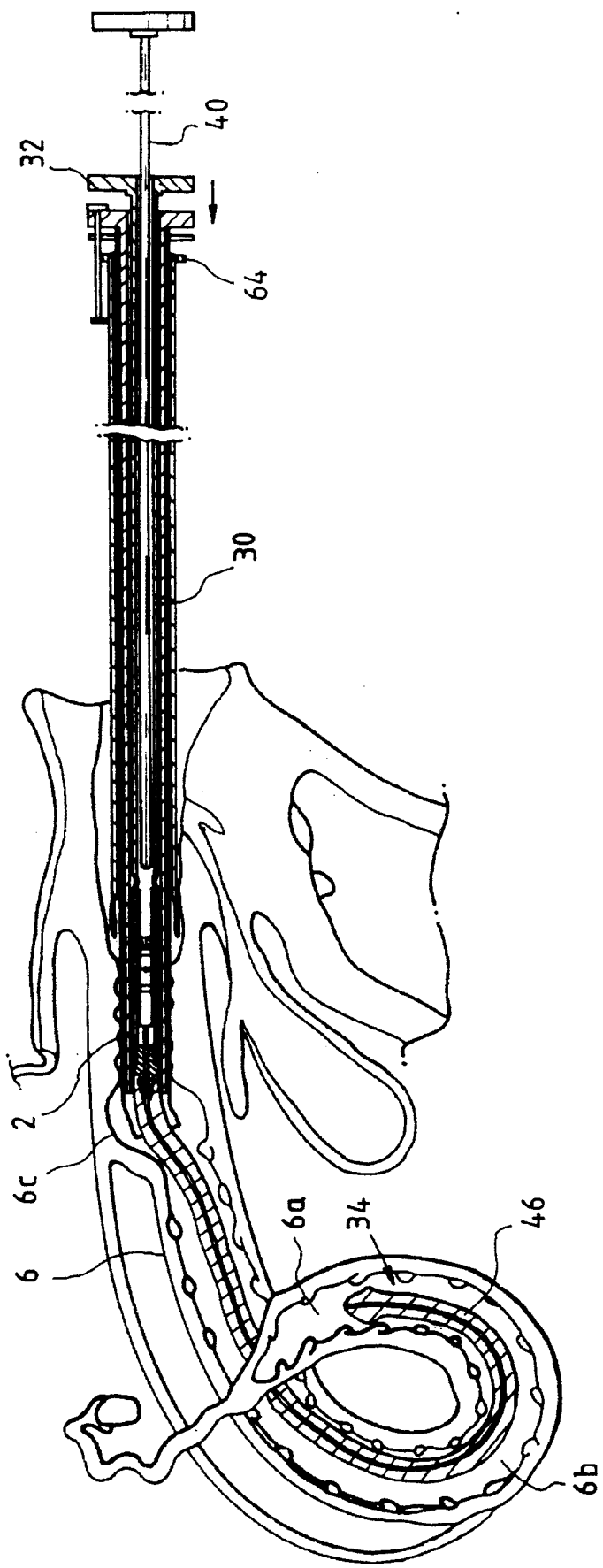

In the instrument of the present invention, generally, a shorter length tip 34 is used for artificial insemination and a longer length tip 34 for embryo transfer (see FIGS. 12, 16 and 24). However, the instrument of the present invention can be employed for both artificial insemination and embryo transfer irrespective of the length of the tip 34 because the tip 34 can be advanced at a desired distance by a proper axial movement of the elongate tube 30 to correspond to various morphologies of the genital organs of the subject. Particularly, although the sperm stored in the straw 38 is ejected at a location of the conical portion 48 of the tip 34 in a rear zone of the cervical canal or a front zone of the uterine cavity during artificial insemination, the ejected sperm moves toward an ampulla of itself and becomes implanted on a uterine wall, thereby obviating any further extension of the tip.

As best shown in FIG. 6, the tip 34 has a boss 54 adapted to fit in the front portion of the straw 38, and a threaded portion 56 rigidly coupled with a thread 72 formed in the proximal end of the elongate tube 30. This rigid coupling structure prevents the tip 34 from being separated from the elongate tube 30 during the withdrawal of the device from the genital organs.

As shown in FIG. 6, the first contamination preventing means 42 includes a hollow cylindrical sheet 58 inserted around the elongate tube 30 and in contact with the tip 34 at its front end, a spring 60 seated in a shoulder 33 of the elongate tube 30 for urging the sheet 58 against the tip 34, and a cylindrical holder 62 secured to the distal end of the elongate tube 30 for retaining the spring 60 in the shoulder 33 of the tube 30. The cylindrical sheet 58 is biased against the tapered portion 50 of the tip 34 by the action of the spring 60 to thereby prevent the penetration of the contaminants existing in the vagina and the cervix thereinto during the insertion of the device into the genital organs. Therefore, this results in the protection of the elongate tube 30 against the contaminants. Additionally, the cylindrical sheet 58 serves to deformably or adjustably support the tip 34. A ring-shaped gripper 70 is movably mounted on the cylindrical holder 62, an end of which is provided with an annular projection 63 for preventing the gripper 70 from escaping therefrom. Furthermore, the outer diameter of the cylindrical sheet 58 is smaller than the maximal diameter of the tip 34 in order to prevent the front end of the cylindrical sheet 58 from injuring the vaginal and the cervical walls during the insertion of the instrument into the genital organs.

As represented in FIG. 6, the second contamination preventing means 44 includes a tubular member 66 surrounding the tip 34 and the sheet 58 and having a rectangular flange 64 formed at its distal end (see FIG. 10), and a fracturable thin film cap 68 welded at a proximal end of the tubular member 66 by an ultrasonic technique for covering the tip 34. Therefore, with the axial forward push of the elongate tube 30 by way of holding the rectangular flange 64 and the gripper 70 by one hand, the thin film cap 68 is ruptured by the tip 34. The structure of the thin film cap 68 will be further discussed hereinbelow.

Figure 7:
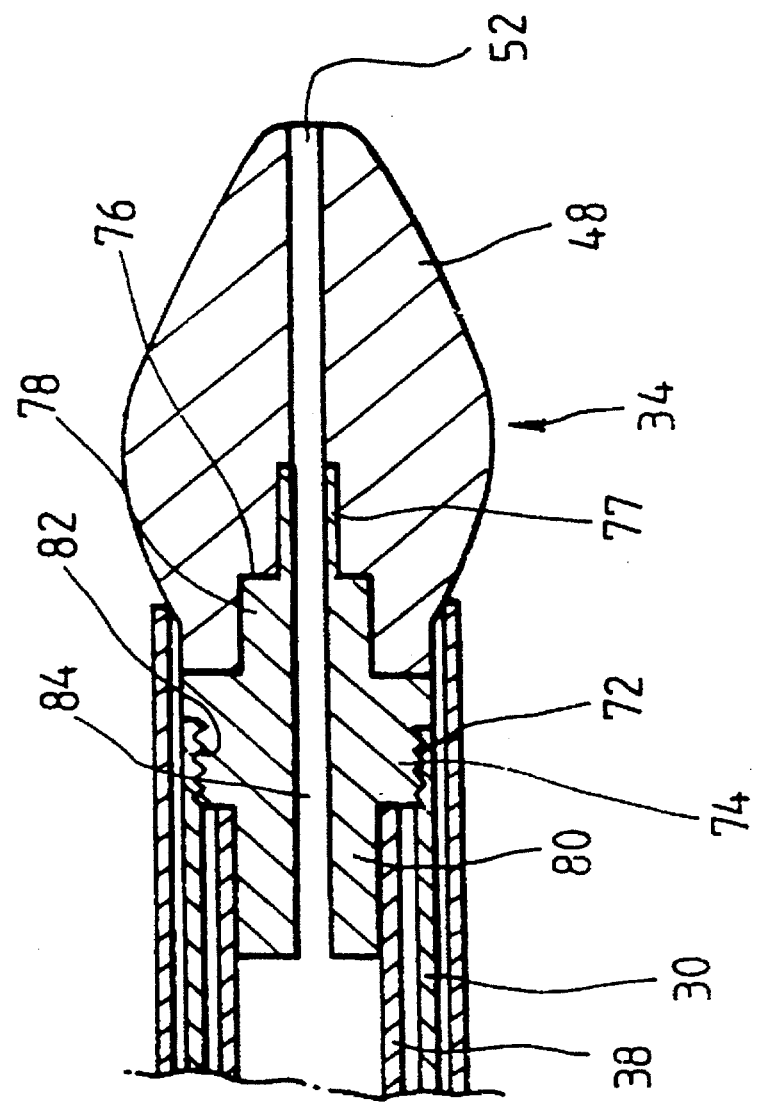
FIG. 7 is a sectional view of a modified coupling of a flexible tip to an elongate hollow tube of the device shown in FIG. 6.

A modified coupling of the elongate tube 30 to the tip 34 is depicted in FIG. 7. In this embodiment, an adapter 74 is interconnected between the elongate tube 30 and the tip 34. The adapter 74 includes a threaded portion 82 formed at its outer surface for engaging with the thread 72 of the elongate tube 30, a boss portion 80 fitted in the front portion of the straw 38, and a stepwise portion 78 coupled to a stepped recess 76 of the tip 34. Further, the adapter 74 has a capillary tube 77 fitted into the passage 52 of the tip 34, which serves to assist the deformation of the tip 34 during the insertion of the instrument into the vaginal and the cervical canals and to provide a rigid connection between the adapter 74 and the tip 34. Preferably, the tip 34 is bonded or thermally welded to the adapter 74 at their recess 76 and stepwise portion 78 by an adhesive or an ultrasonic technique so as to prevent the separation of the tip 34 from the adapter 74. Additionally, the adapter 74 has a through hole formed therein, which is in communication with the straw 38 and the passage 52 of the tip 34.

Figure 8:
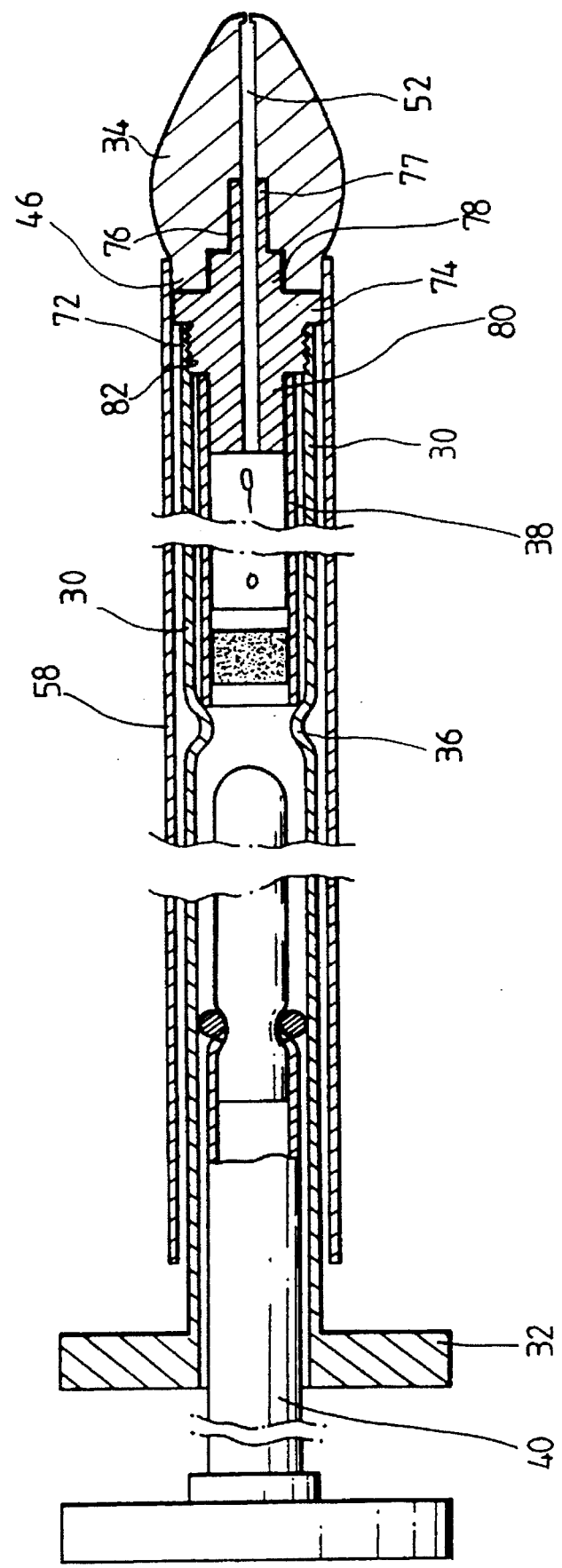
FIG. 8 is a sectional view of an alternative engagement of the tip with a hollow cylindrical sheet of a first contamination preventing means of the device depicted in FIG. 6.

FIG. 8 illustrates a modification of the first contamination preventing means of the device in accordance with the present invention wherein the coupling of the tip 34 with the elongate tube 30 is generally similar to that depicted in FIG. 7 and, therefore, will not be further described herein. In this preferred embodiment, the front end of the cylindrical sheet 58 of the first contamination preventing means 42 is thermally welded to both the outer surface of the adapter 74 and an outer periphery of the tip 34 by an appropriate technique. Therefore, this modified contamination preventing means does not have the spring 60 for urging the cylindrical sheet 58 against the tip 34, and the holder 62 for retaining the spring 60 in the shoulder 33 of the elongate tube 30 as shown in FIG. 6. In assembling the contamination preventing means 42 with the elongate tube 30, the cylindrical sheet 58 integral with the adapter 74 and the tip 34 is inserted around the elongate tube 30 in which the straw 38 has already been mounted. Thereafter, with the gripping of a rear portion of the cylindrical sheet 58 by hand, rotating of the sheet 58 enables the threaded portion 82 of the adapter 74 to engage with the thread 72 of the elongate tube 30, with the boss portion 80 of the adapter 74 being fitted in the straw 38. As a result, the contamination of the tip 34 and a front portion of the sheet 58 is prevented during the assembling process of the device. Further, the tip 34 can be easily assembled with the elongate tube 30 via the adapter 74.

Figure 9:
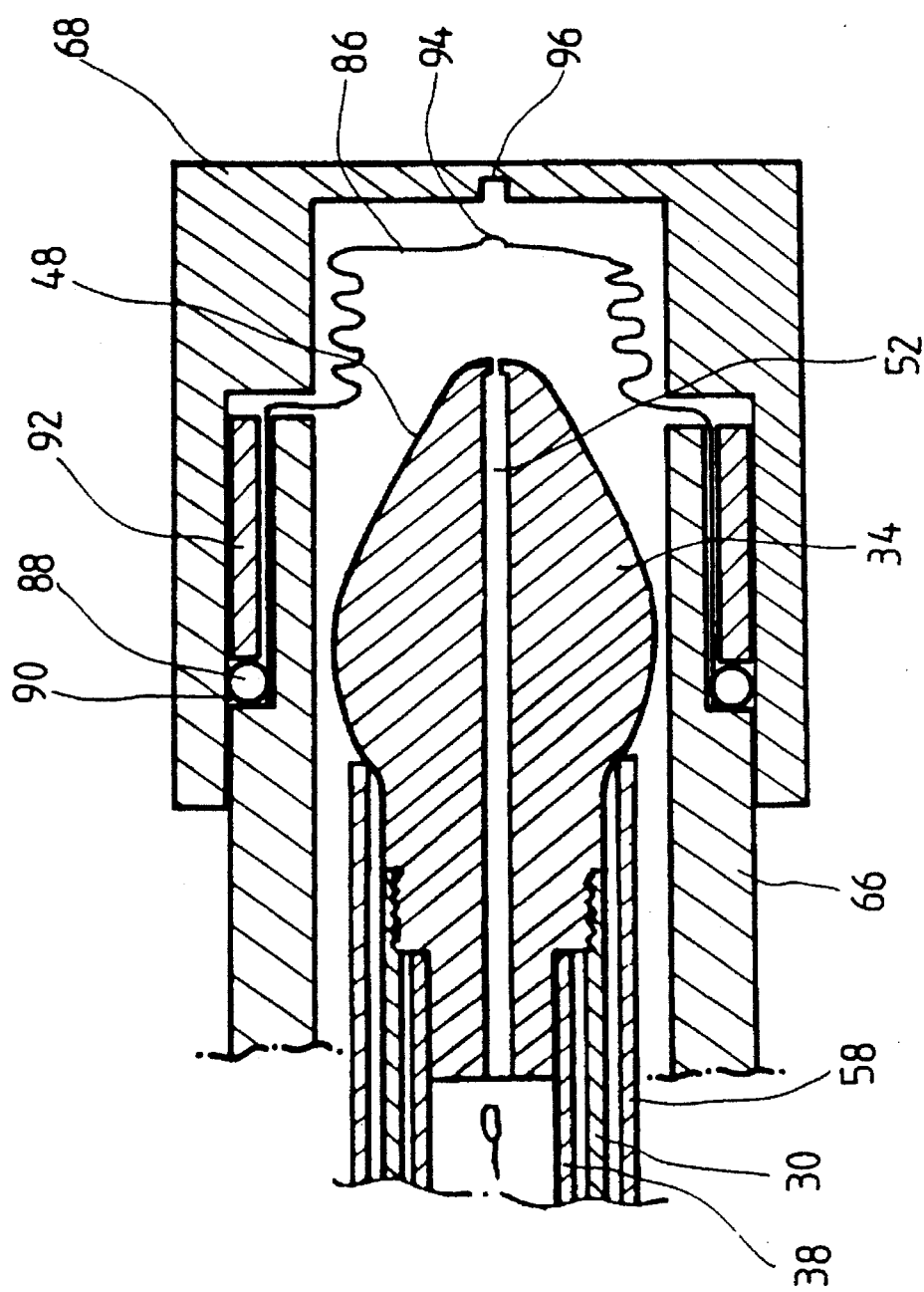
FIG. 9 is a sectional view of another embodiment of a second contamination preventing means of the device shown in FIG. 6.

FIG. 9 shows another embodiment of the second contamination preventing means of the device, wherein a stretchable thin capsule 86 is secured to the proximal end of the tubular member 66 at its open end and disposed inside the thin film cap 68 for protecting the tip 34 from any contaminants. The thin capsule 86 has an annular projecting ring 88 provided at the open end thereof, which rests on a stepped shoulder 90 of the proximal end of the tubular member 66. The thin capsule 86 is tightly fixed to the stepped shoulder 90 of the tubular member 66 by way of a fixture, e.g., a ring 92. In addition, the thin capsule 86 is provided with a breakable portion 94 integrally formed at its close end and arranged in a substantially coaxial relationship with the passage 52 of the tip 34, which can be ruptured after the stretching of the capsule by the axial advancement of the tip 34. On the other hand, the thin film cap 68 is thermally welded to the proximal end of the tubular member 66 to cover the thin capsule 86. Therefore, e.g., after the device reaches an entrance of the cervical canal through the vaginal canal during artificial insemination or embryo transfer, the pushing of the elongate tube 30 enables the tip 34 to move forward, thereby rupturing the thin film cap 68. Sequently, the tip 34 is enwrapped with the stretchable thin capsule 86 by its forward movement and passes through the cervical canal. The tip 34 is thus introduced into the uterine cavity, being enwrapping with the stretchable thin capsule 86. Thereafter, with the continuous pushing of the elongate tube 30, the breakable portion 94 of the thin capsule 86 is torn by the tip 34, enabling the tip 34 to be exposed in the uterine cavity through the torn opening of the thin capsule 86. Preferably, the thin capsule 86 is ruptured at the location of the tip 34 in a middle area of the cervical canal during the artificial insemination and at the location of the tip 34 in the uterine cavity or the uterine horn during the embryo transplantation. This can be adjusted by varying the stretchiness of the thin capsule 86. As discussed above, in accordance with the preferred embodiment of the present invention, the stretchable thin capsule 86 encloses the tip 34 and a portion of the cylindrical sheet 58 during the insertion of the device into the genital organs of the female subject, thereby protecting them from germs and impurities in the vaginal and the cervical canals. As a result, the sperm or embryo ejected from the straw 38 of the device is delivered to the uterine cavity or the uterine horn under an aseptic condition.

Figure 10:
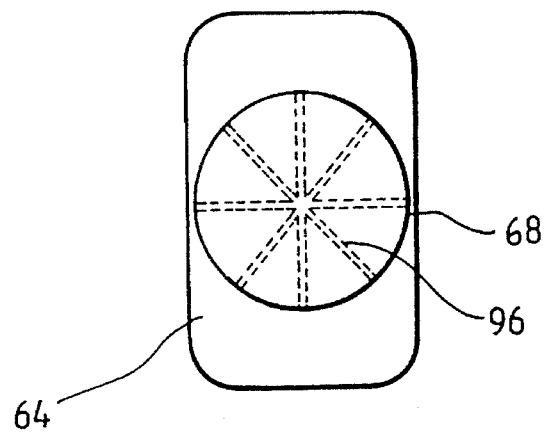
FIG. 10 is a right side view of the device of FIG. 6.

As shown in FIG. 10, the thin film cap 68 is provided with a plurality of radial tearing lines 96 which can be easily ruptured by a forward movement of the tip 34. However, if any fragment thereof occurs during the rupturing of the thin film cap 68, it may adhere to the conical portion 48 of the tip 34 due to the static electricity or cervical mucus and be introduced into the uterine cavity, causing the obstruction of the embryonic growth. Therefore, the thin film cap 68 is preferably made of an stretchable elastic material so as to prevent any occurrence of a broken fragment from the ruptured thin film cap 68.

Figure 11:
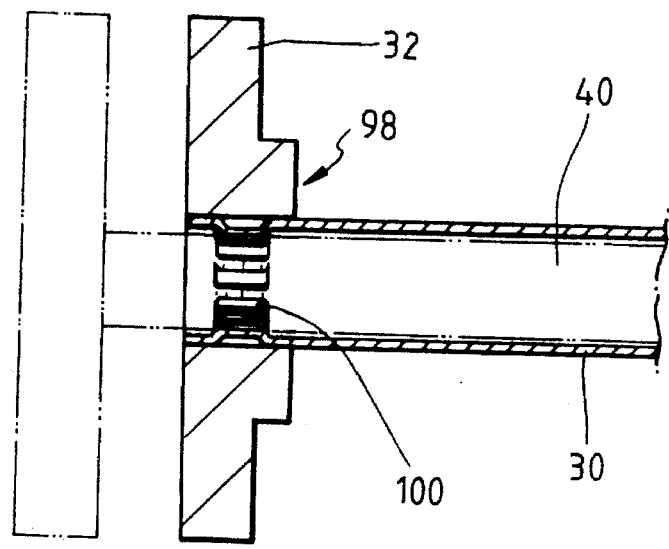
FIG. 11 is a sectional view of a modified restraining means of a piston rod of the device.

FIG. 11 represents modified restraining means for preventing the piston rod 40 from freely sliding within the elongate tube 30. In this embodiment, the elongate tube 30 has an annular spring-like element 100 formed at its distal end by a stamping or pressing technique, which exerts a pressure on the piston rod 40 to thereby restrain the free movement of the piston rod 40 within the elongate tube 30.

In accordance with a preferred embodiment of the invention, the procedure of artificial insemination of an animal by employing the device of FIG. 6 will be now described hereinbelow, with reference to FIGS. 18 to 20. It should be understood that a various combination of the inventive features present in the instant invention can be usefully employed for the artificial insemination or embryo transplantation.

Figure 18:
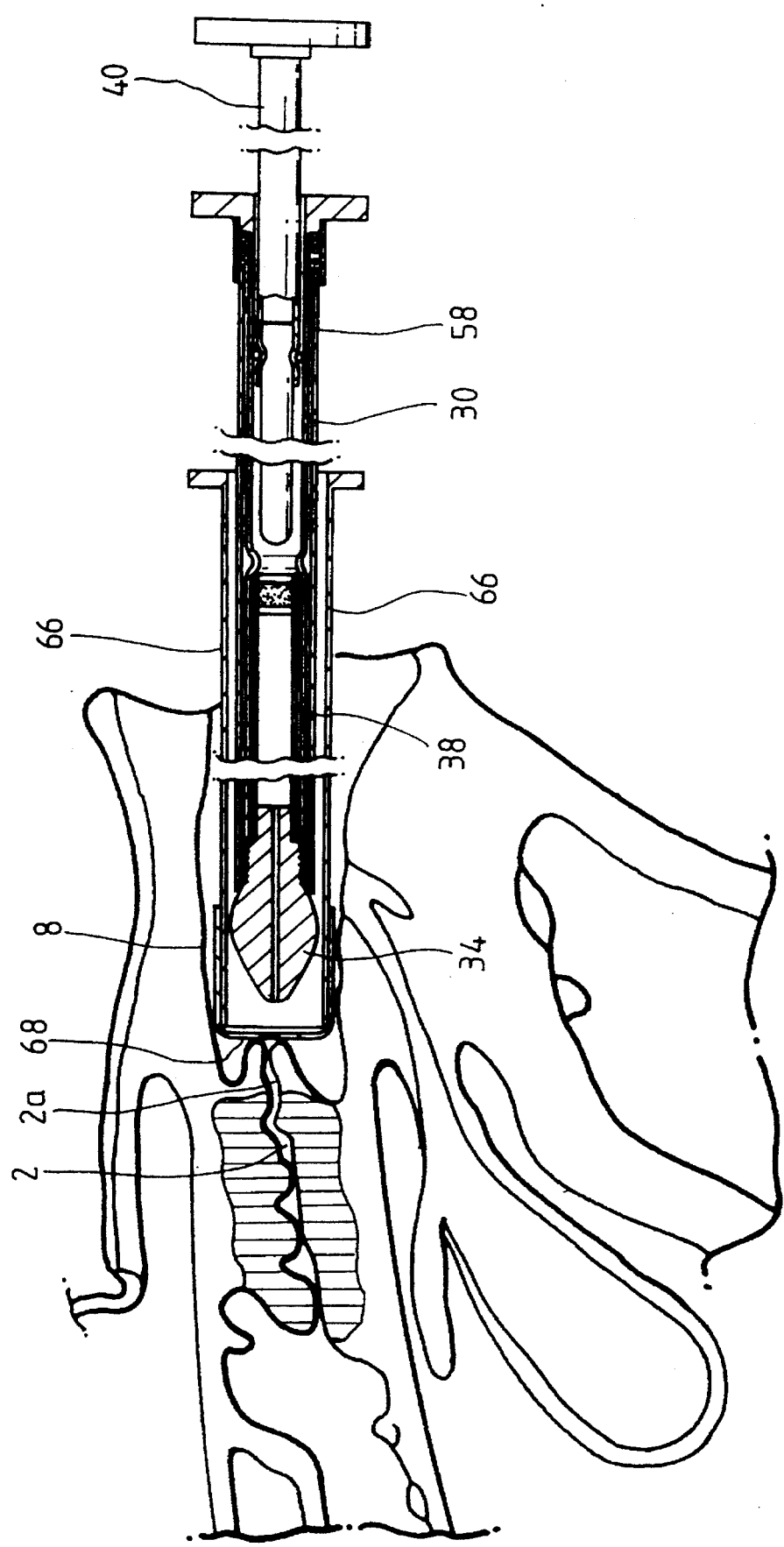
FIGS. 18 to 20 provide the procedure of artificial insemination of an animal by using, e. g., the device for transferring sperm or embryo shown in FIG. 6.

As shown in FIG. 18, the assembled device with the straw 38 storing the sperm therein is inserted into the vaginal canal 8 until the thin film cap 68 contacts with the entrance 2a of the cervical canal 2. At this time, the tubular member 66 and the thin film cap 68 surround the tip 34 and the cylindrical sheet 58, shielding them from impure materials and viruses in the vagina 8.

Figure 19:
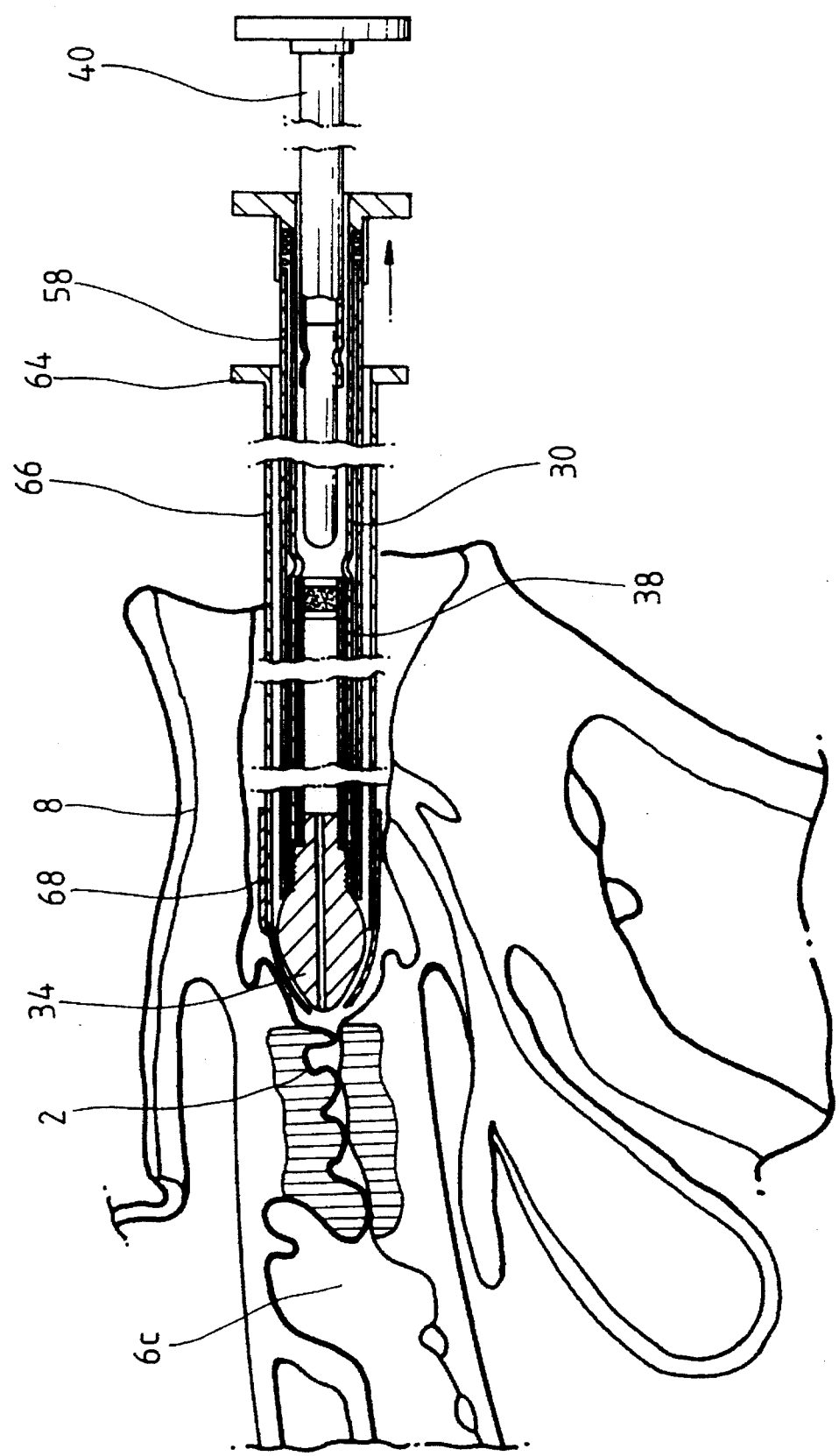

Thereafter, as shown in FIG. 19, with the gripping of the rectangular flange 64 of the tubular member 66 by hand, the elongate tube 30 is pushed toward the cervical canal, simultaneously with the tip 34 being inserted into the cervical canal 2 together with the thin film cap 68. In this case, the thin film cap 68 conforms to the configuration of the conical portion 48 of the tip 34 without the rupture thereof. Therefore, this results in the protection of the tip 34 and cylindrical sheet 58 from infectious and impure materials existing in the cervical canal.

In sequence, a further pushing of the elongate tube 30 will cause the tip 34 to rupture the thin film cap 68 without the creation of any fragment because of the elasticity and the radial tearing lines of the film cap 68 and to advance sufficiently into the cervical canal. At this time, the cylindrical sheet 58 still encloses the elongate tube 30 while maintaining the inserting skate of the device in the cervical canal 2, thereby preventing the penetration of mucus, viruses and impurities which may be present in the cervical canal into the elongate tube 30. In particular, the inner diameter of the outlet port 52a of the passage 52 of the tip 34 is smaller than that of the inlet port 52b of the tip 34 to thereby minimize the ingression of the cervical mucus into the passage of the tip 34. Accordingly, the tip 34 is introduced into the uterine cavity without the contamination thereof, preventing the sperm contamination. This results in the enhancement of the rate of pregnancy by artificial insemination.

Further, as described above, since the tip 34 is made of a deformable material and has the conical front portion 48, it tends to warp or bend along the meanders of the cervix and, therefore, passes through the cervical canal with ease without injuring the cervical wall. For this reason, in the present invention, an expander for spreading the cervical canal is not needed to insert the device into the cervix. In addition, the outer diameter of the cylindrical sheet 58 is smaller than the maximal diameter of the tip 34 to thereby enable the cylindrical sheet 58 to easily enter into the cervical canal without damaging the cervical wall.

Figure 20:
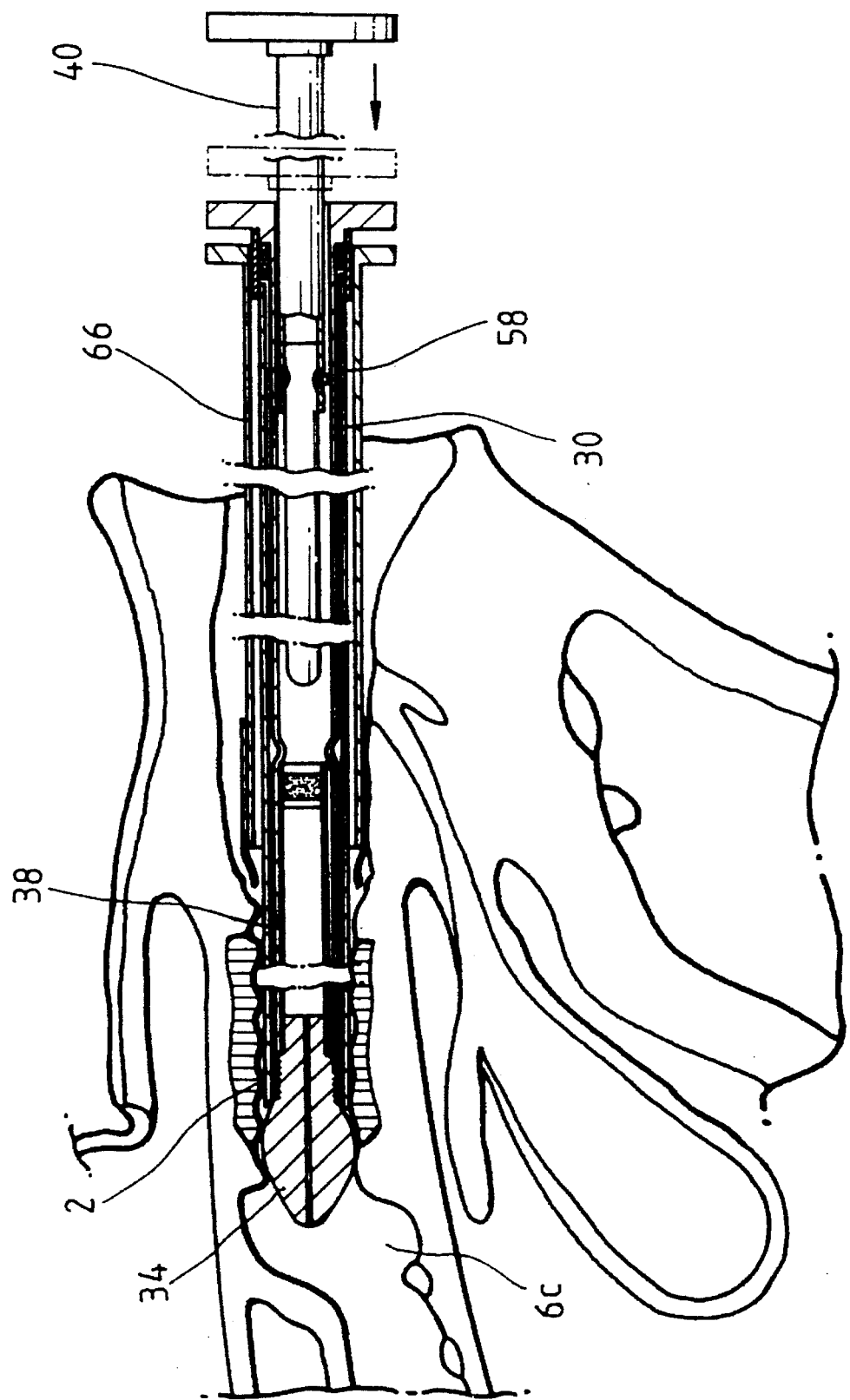

Thereafter, as depicted in FIG. 20, when the tip 34 reaches the front zone of the uterine cavity or the uterine horn, which can be felt by hand inserted into the rectum of the animal subject, the forward movement of the elongate tube 30 is stopped, while the piston rod 40 is pushed to discharge the sperm stored in the straw 38 into the uterine cavity or horn, achieving the artificial insemination. In case of embryo transfer, the tip 34 is introduced into the rearmost zone 6a of the uterine horn 6 and then the embryo contained in the straw is discharged by the pushing off the piston rod 40.

After artificial insemination has been completed, the device is withdrawn from the genital organs of the female subject, during which time the tip 34 remains undetached from the elongate tube 30 due to their rigid coupling. Further, with the replacement of the tip 34, the straw 38, the cylindrical sheet 58 and the tubular member 66 with fresh ones, the device is reusable without administering any sterilization or disinfection thereof.

Referring now to FIG. 12, there is provided another preferred embodiment of the instrument for artificial insemination and embryo transfer in accordance with the present invention. This preferred instrument is designed to be preferably useful for embryo transplantation, although it can be employed in the artificial insemination as well.

Figure 25:
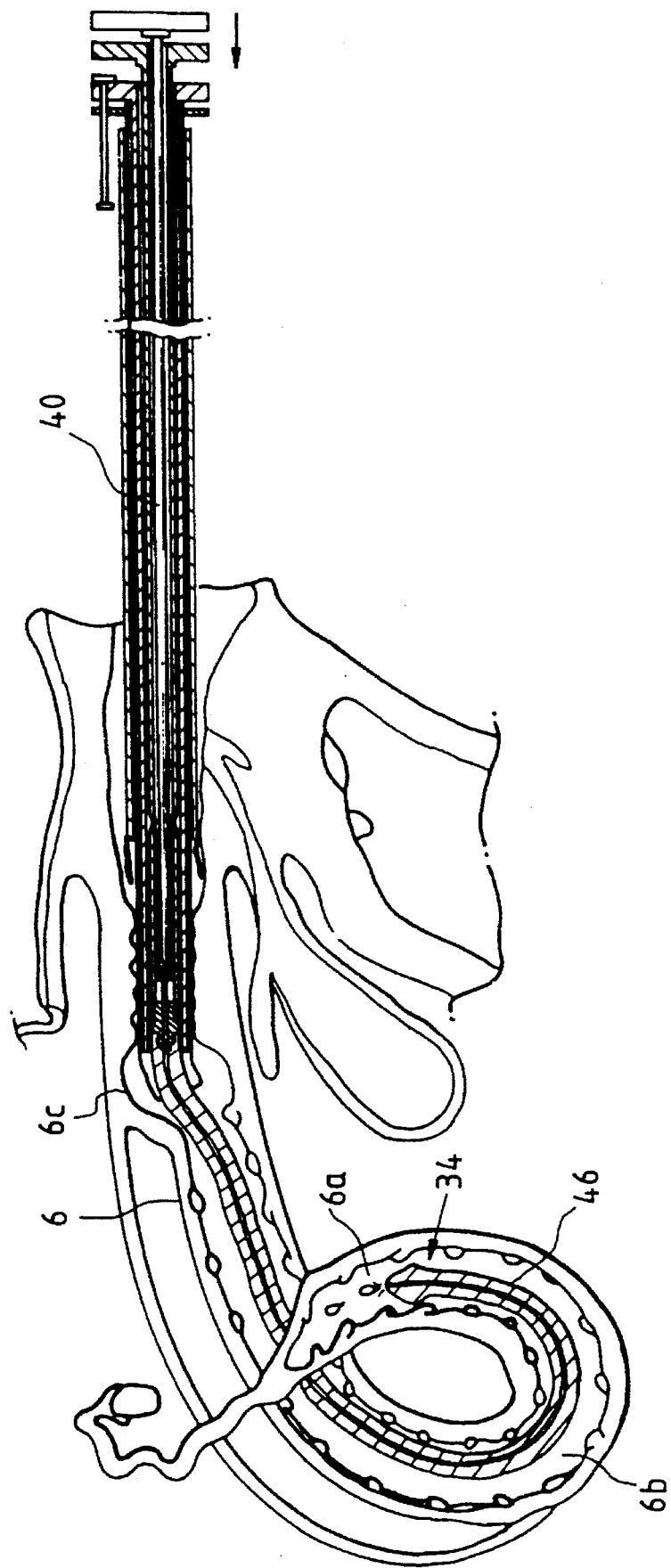

As shown in FIG. 12, coupled to the proximal end of the elongate tube 30 via the adapter 74 is the tip 34 which has a relatively long main body .46 for the purpose of reaching the rearmost zone of the uterine horn for the embryo transplantation (see FIGS. 24 and 25). The length of the tip 34 can be adjusted to conform to various sizes of the uterine horn of the animal subjects. A support sleeve 102 houses the elongate tube 30 and the main body 46 of the tip 34 therein and is in contact with the tapered middle portion 50 at its front end for supporting the tip 34 so as to allow the deformation of the tip 34 during the passing of the tip 34 through the cervical canal. In addition, the support sleeve 102 has a flange 104 provided at its rear end. The outer diameter of the support sleeve 102 is made smaller than the maximal diameter of the tip 34 to prevent the support sleeve from injuring the cervical wall while passing through the cervix. In this embodiment, the first contamination preventing means includes a flexible tube 106 suitable for enclosing the tip 34 and the support sleeve 102 so as to prevent them from being contaminated by impure materials and viruses in the cervical canal during the passing of the device through the cervix. One end of the flexible tube 106 is in contact with the flange 104 of the support sleeve 102, while the other end of the sleeve 106 is folded at 108 in the tubular member 66 of the second contamination, preventing means 44 to close its opening 110. Further, inserted around the flexible tube 106 is the second contamination preventing means 44 which is substantially similar to that shown in FIG. 6. Also, any one of the coupling structures of the tip 34 with the elongate tube 30, the straw 38 or the adapter 74 as illustrated in FIGS. 6, 8 and 16 can be employed in this preferred instrument in a similar manner.

On the other hand, in case of the embryo transfer in an animal having a rather long uterine horn, the distance between the flange 104 of the support sleeve 102 and the flange 32 of the elongate tube 30 or the flange 64 of the tubular member 66 can be further extended from each other. Therefore, as shown in FIG. 12, the support sleeve 102 is provided with a gripping means 114 for holding the respective flanges 32, 64 and 104 by one hand. The gripping means 114 includes a mounting plate 116 slidably inserted around the flexible tube 106 of the first contamination preventing means 42 and disposed between the flange 64 of the tubular member 66 and the flange 104 of the support sleeve 102. A sliding bar 122 is engaged with a hole 118 of the flange 104 of the support sleeve 102 and an aperture 120 of the mounting plate 116; and has grip rings 124 carried by its ends. The operation of the gripping means 114 will be further discussed hereinbelow.

Figure 13:
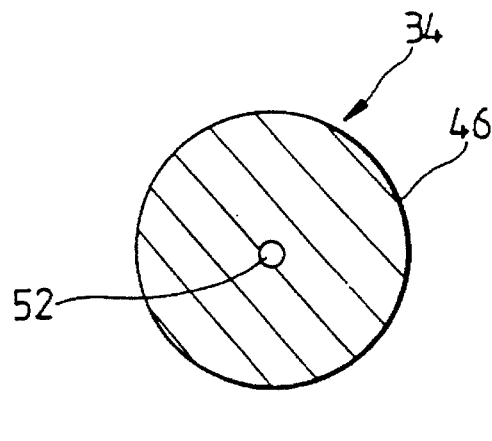
FIG. 13 is a vertical sectional view of a flexible tip shown in FIG. 12.

As represented in FIG. 13, the main body 46 of the tip 34 is constructed of a circular shape in cross-section. In case that the tip 34 is relatively short in length, it is not necessary to embed reinforcing wires in the tip 34. In the long extending tip 34, the reinforcing wires may preferably be embedded in the tip 34 for the purpose of adjusting the flexibility of the tip 34.

Figure 14:
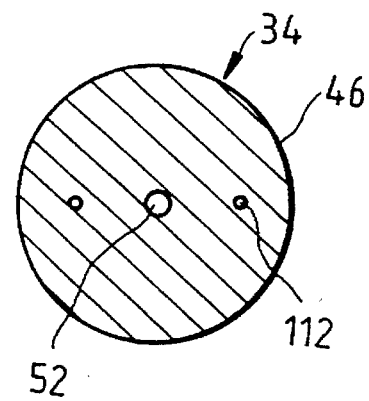
FIG. 14 is a view similar to that of FIG. 13 but illustrates an alternative flexible tip having reinforcing wires embedded therein.

Referring to FIG. 14, embedded in the main body 46 of the tip 34 are the reinforcing wires 112 which are apt to restrict an excessive bending of the tip 34 during the passing of the tip through the uterine horn as discussed above. However, since the flexibility and bending of the tip 34 can be adjusted by varying the length, configuration and material of the tip 34 depending on the size and shape of the genital organs of the animal subject, it should be understood that the embedding of the reinforcing wires in the tip 34 is not always required.

Figure 15:
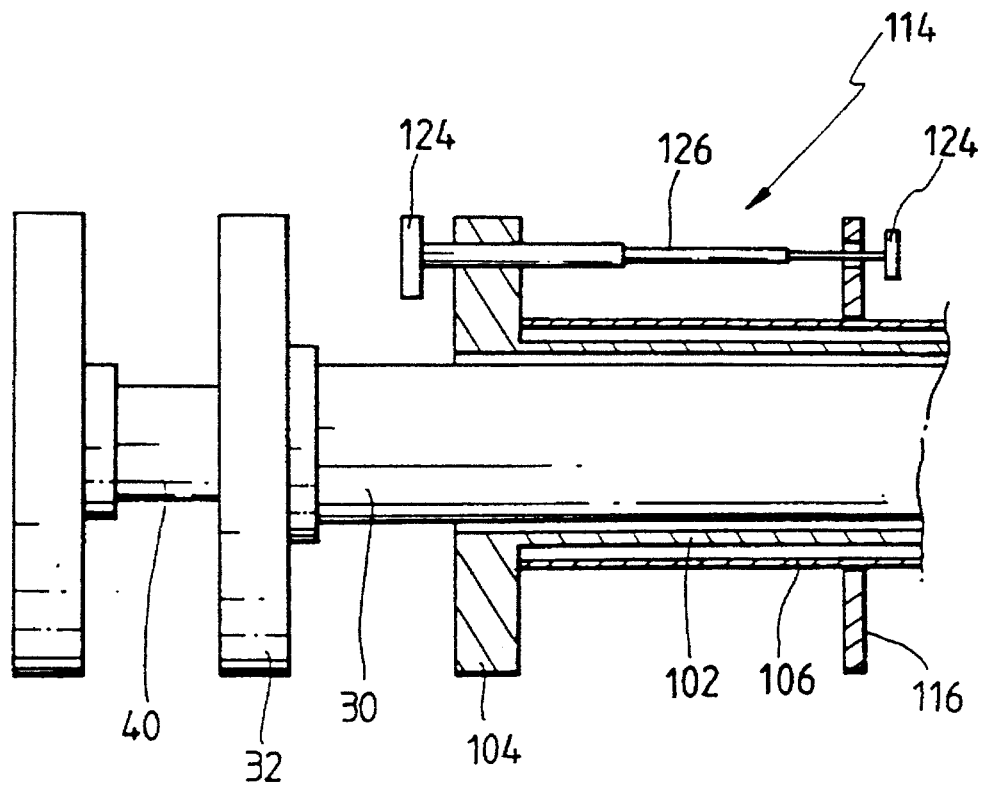
FIG. 15 represents another gripping means of the device of FIG. 12.

A modified gripping means 114 is shown in FIG. 15 wherein a bar 126 of the gripping means 114 is made of a telescopic structure. The telescoping of the bar 126 renders it easier to handle the device and to grip the elongate tube 30, the tubular member 66 and the support sleeve 102 irrespective of the size of the uterine horn of the animal.

FIG. 16 illustrates a further modified device for artificial insemination and embryo transfer of the invention. This modified device is generally similar to that of FIG. 12 except that the second contamination preventing means 44 shown in FIG. 9 replaces that of FIG. 12; and the flexible tube 106 of FIG. 12 is removed from the modified device. In this embodiment, the main body 46 of the tip 34 is thermally welded in a recess 75 of the adapter 74 threadedly coupled to the proximal end of the elongate tube 30. In spite of the removal of the first contamination preventing means 42, i. e., the flexible tube 106, the front end of the support sleeve 102 maintains its contact with the tapered portion 50 of the tip 34 to thereby prevent the contamination of the elongate tube 30.

Figure 17:
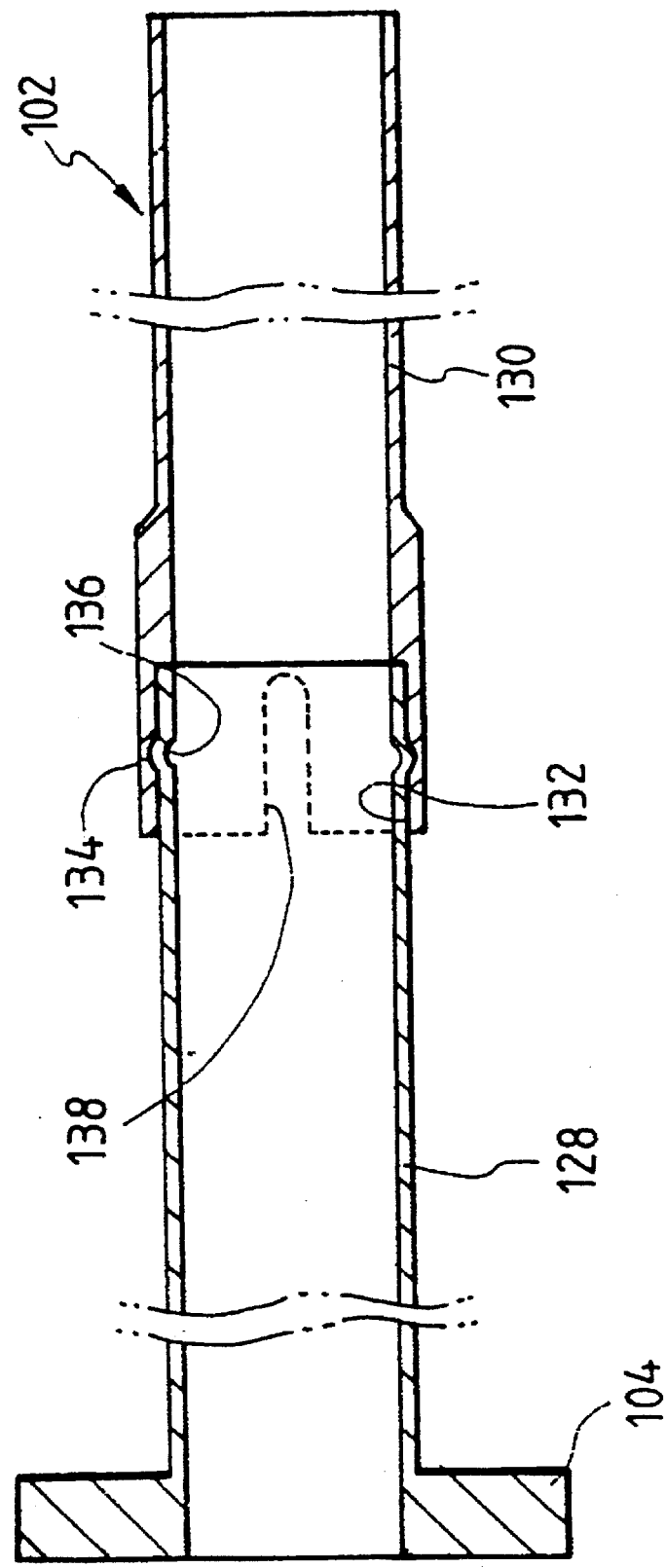
FIG. 17 is a sectional view of an alternative support sleeve of the device shown in FIG. 16.

An alternative structure of the support sleeve of FIG. 16 is shown in FIG. 17. This support sleeve 102 consists of two parts 128, 130 assembled together. That is, an end portion of the first part 128 is separably fitted in a stepped portion 132 of the second part 130 of the support sleeve 102. The first part 128 of the support sleeve 102 has an annular projection 136 formed at the end portion thereof, which is held in an annular indent 134 of the stepped portion 132 of the second part 130. Further, provided at the stepped portion 132 of the second part 130 is at least one slit 138 which serves to facilitate the fitting of the first part 128 in the stepped portion 132 of the second part 130. In accordance with this preferred embodiment, when the device passes through the vaginal and the cervical canals, the first part 128 of the support sleeve 102 is shielded from the contaminants in the canals by means of the tubular member 66, while the second part 130 of the sleeve 102 is subjected to the contaminants. Therefore, the contaminated part 130 is removed from the support sleeve 102 after artificial insemination or embryo transfer and then replaced with a new one. As a result, the first part 128 of the support sleeve 102 can be repeatedly used without the sterilization thereof.

Figure 21:
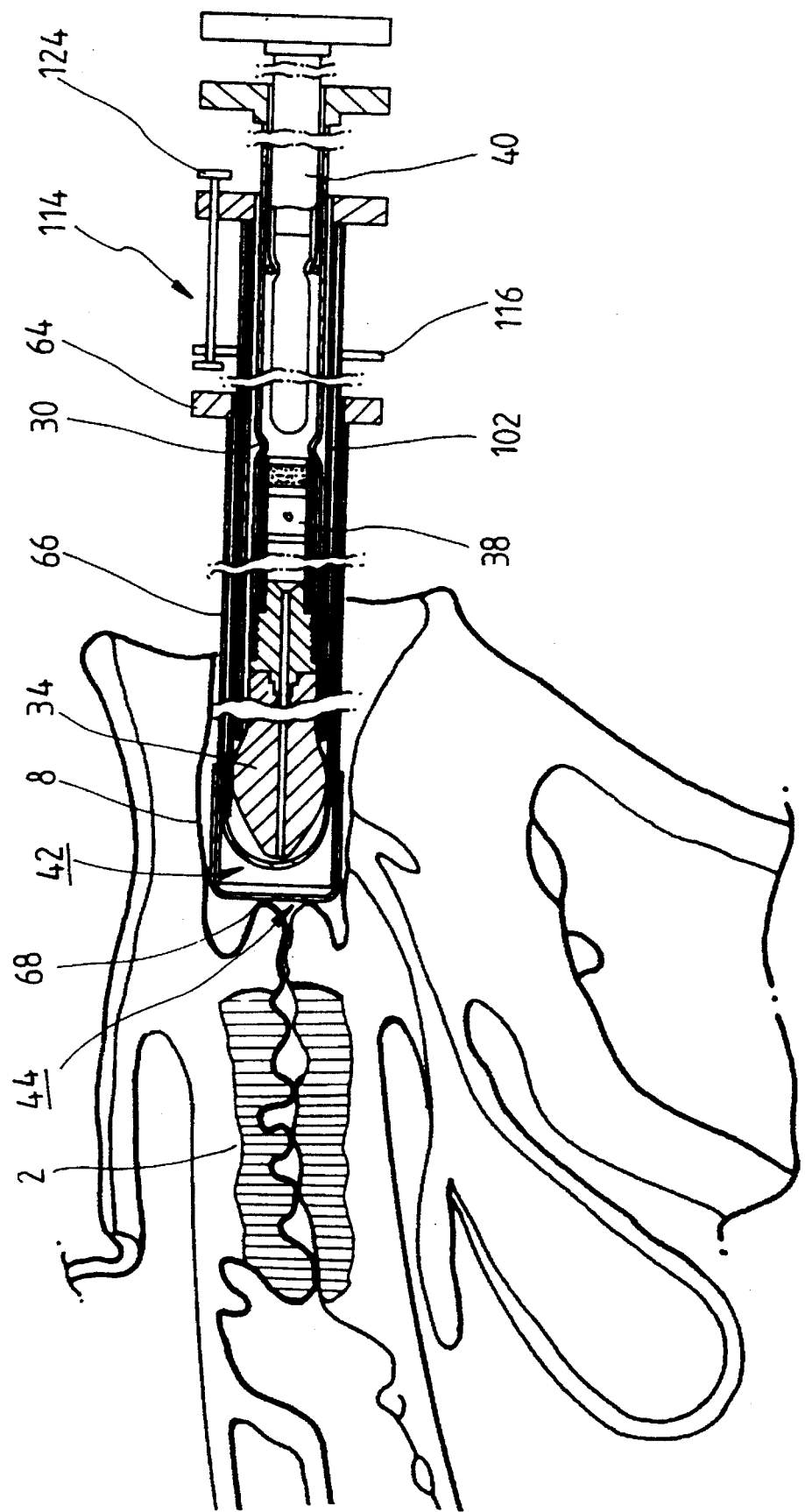
FIGS. 21 to 25 offers the procedure of embryo transplantation of an animal by using, e.g., the device for transferring sperm or embryo represented in FIG. 12.

Furthermore, with reference to FIGS. 21 to 25, the procedure of the embryo transfer of the animal by using one of the afore-mentioned devices will be described hereinafter. An embryo to be transferred is stored in the straw 38 together with a medium liquid, which, in turn, is loaded in the embryo transfer device. Thereafter, as depicted in FIG. 21, the device is inserted into the vaginal canal of the animal so that the thin film cap 68 of the second contamination preventing means 44 is positioned at the entrance 2a of the cervical canal 2. While maintaining the device at this location, the flexible tube 106 of the first contamination preventing means 42 is enclosed with the tubular member 66 and the thin film cap 68 to prevent it from being contaminated by viruses, impure materials and the like in the vaginal canal.

Figure 22:
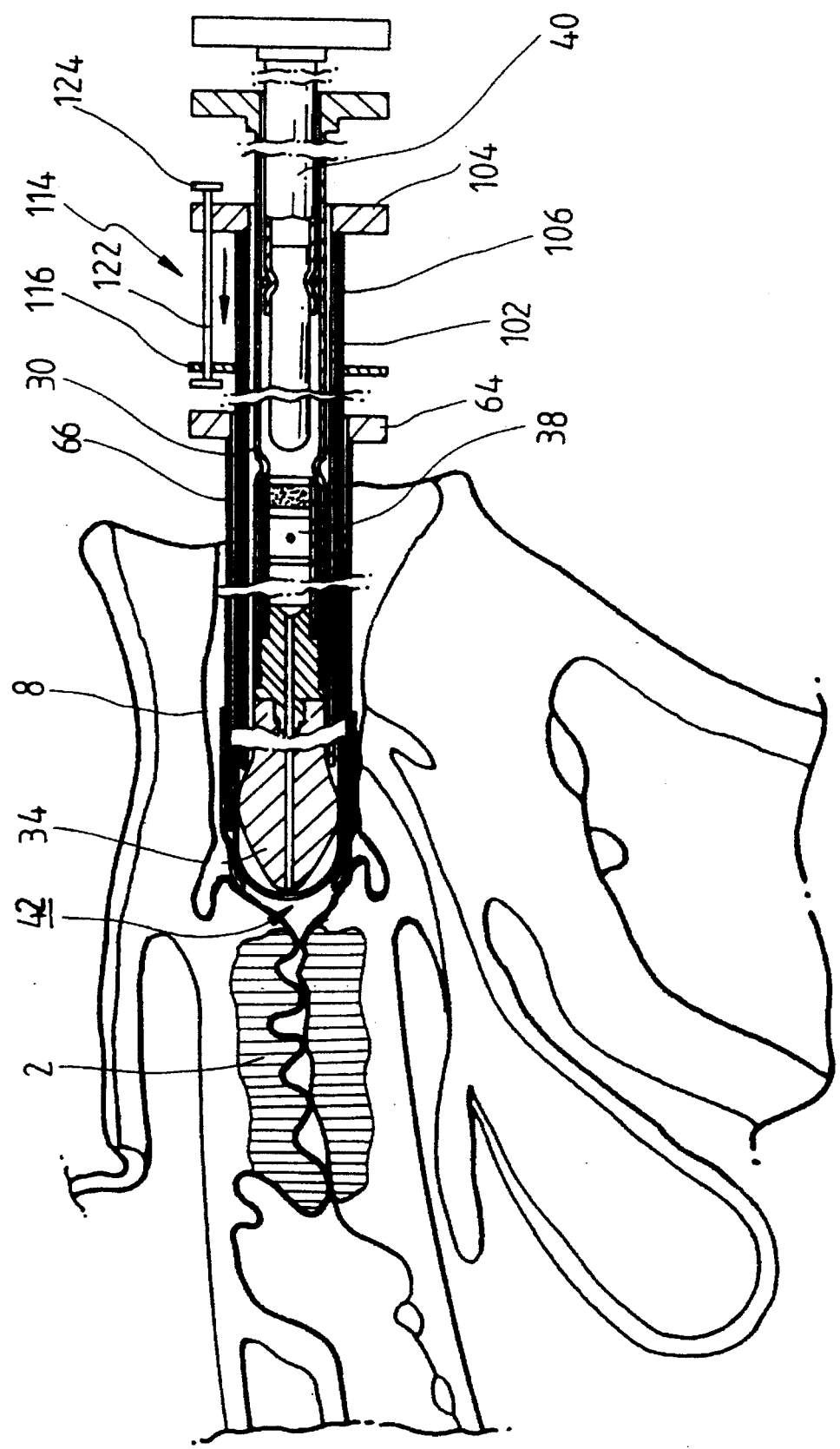

And then, as shown in FIG. 22, the mounting plate 116 is moved adjacent to the flange 64 of the tubular member 66 at the same time of contacting the grip ring 124 of the sliding bar 122 with the flange 104 of the support sleeve 102. At this time, with the holding of the flange 64 of the tubular member 66 by an index and a middle fingers, pushing of the mounting plate 116 by a thumb finger causes the support sleeve 102 to move forward, with the tip 34 being advanced toward the thin film cap 68. As a result, the film cap 68 is stretched and then ruptured along its tearing lines 96 by a further forward movement of the tip 34 without producing any broken fragment. Therefore, the flexible tube 106 of the first contamination preventing means 42 contacts with the cervical wall upon the rupture of the thin film cap 68 but still encloses the tip 34 and the support sleeve 102 to thereby prevent them from being contaminated during the passing of the flexible tube 106 through the cervical canal 2.

On the other hand, in case that the device comprising the contamination preventing means 44 with the stretchable thin capsule 86 (see FIG. 9), with the flexible tube 106 being removed from the device, is used for embryo transfer, with the further pushing of the tip 34 at the rupture of the thin film cap 68, the tip 34 is wrapped with the thin capsule 86 and enters into the cervical canal. Further, the continuous advancement of the tip 34 causes the capsule 86 to be torn at its breakable portion 94. As a result, the tip 34 passes through the torn opening of the capsule 86 and becomes exposed to the uterine cavity in an aseptic state.

Figure 23:
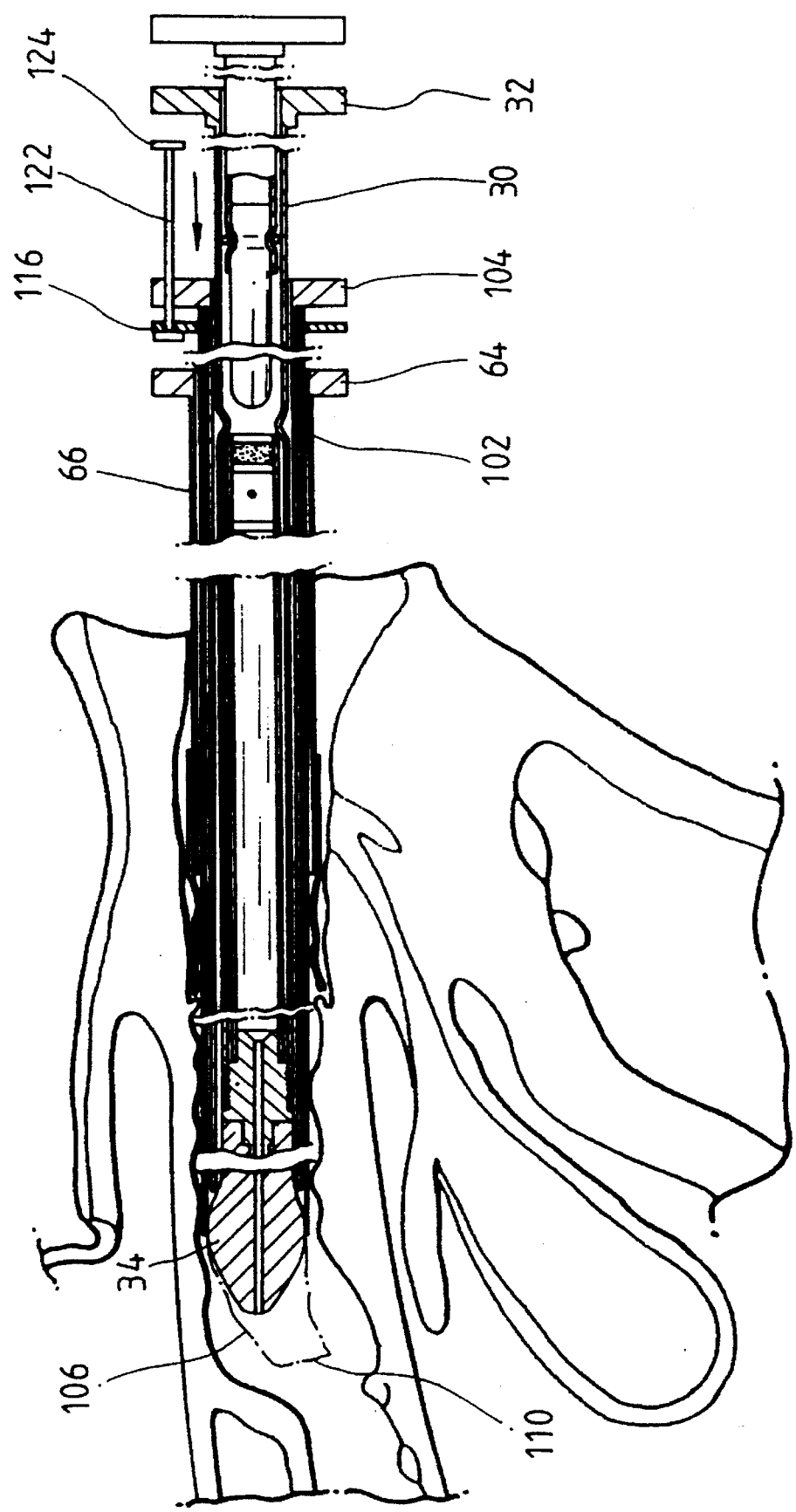

As shown in FIG. 23, when the support sleeve 102 is pushed forward along the cervical canal 2, it supports deformably or flexibly the tip 34 and enters into the cervical canal with ease because the maximal diameter of the tip 34 is greater than the outer diameter of the sleeve 102. Further, since the tip 34 is made of a flexible and deformable material and constructed of a conical configuration at its front portion, with the bending of the tip 34 in conformity with the sinuous shape of the cervical wall, it passes through the cervical canal without causing lesions to the cervical wall.

Further, when the tip 34 reaches the uterine cavity 4 or the front zone 6c of the uterine horn 6, the end of the flexible tube 106 folded at 108 becomes open, thereby exposing the tip 34 to the uterine cavity or horn without the contamination thereof. This results in the prevention of the contamination of the embryo. Thereafter, the tip 34 is led to one of the uterine horns by hand inserted into the rectum of the animal. Upon the location of the tip 34 at the one of the uterine horns, the forward movement of the support sleeve 102 is ceased while the tip 34 commences to be drawn out of the support sleeve 102 by the forward pushing of the elongate tube 30 at the same time of holding the flanges 32, 104 of the elongate tube 30 and the support sleeve 102 with fingers. On the other hand, a relatively extended distance between the flange 32 of the elongate tube 30 and the flange 104 of the support sleeve 102 may render it difficult to push forward the elongate tube 30 by one hand. In such case, the mounting plate 116 is retreated from the rectangular flange 64 of the tubular member 66 so as to maintain a contact with the flange 104 of the support sleeve 102; and the sliding bar 122 of the gripping means 114 is pulled toward the flange 32 of the elongate tube 30. Further, the tubular member 66 is rotated at about 90 degrees so that the rectangular flange 64 of the tubular member 66 does not interfere with the advancement of the sliding bar 122 during the forward movement of the elongate tube 30 (see FIG. 24). Thereafter, with the holding of the flanges 32 of the elongate tube 30 and the grip ring 124 of the sliding bar 122 by fingers, the elongate tube 30 is pushed in the forward direction with respect to the support sleeve 102. As discussed above, this device can be easily manipulated by one hand without an assistance of another operator.

As shown in FIG. 24, a further pushing of the elongate tube 30 will cause the tip 34 to be gradually drawn from the support sleeve 102, thereby making it possible to introduce the conical portion 48 of the tip 34 into the desired rearmost zone 6a of the uterine horn 6, which is generally the natural implanted area of the embryo. In this case, the main body 46 of the tip 34 tends to warp to conform with the shape of the uterine horn due to its flexibility, advancing smoothly the tip 34 along the uterine horn without causing any damage to the wall of the uterine horn. In addition, when the operator feels the tip 34 located at the rearmost zone of the uterine horn by his hand, the advancement of the tip 34 is stopped.

Consequently, as shown in FIG. 25, with the axial pushing of the piston rod 40, a front portion of the piston rod 40 is inserted into the straw 38 along the annular radial ridge 36 of the elongate tube 30, injecting the embryo and the medium liquid stored in the straw 38 into the rearmost zone 6a of the uterine horn 6. In particular, the injected embryo does not normally adhere to the tip 34 due to the provision of the passage 52 at the front conical portion 48 of the tip 34. This results in the better rate of pregnancy.

Upon the completion of the embryo transfer, the device is removed from the female subject without the separation of the tip 34 from the elongate tube 30 due to their rigid coupling structure. Thereafter, the tip 34, the straw 38, the tubular member 66 and the flexible tube 106 are separated from the device and replaced with new ones. Therefore, the remaining elements of the device can be repeatedly used without the sterilization thereof.

Otherwise, in case of using the support sleeve 102 consisting of the detachable parts 128, 130 (see FIG. 17) without the employment of the flexible tube 106, with the replacement of the contaminated part 130 with a sterilized one, the part 128 of the support sleeve 102 is reusable without the disinfection thereof.

The modified devices of the present invention are primarily intended to be useful for embryo transfer but can also be employed for artificial insemination of animals or embryo transfer and artificial insemination of humans. In case of artificial insemination, when the tip 34 of the device reaches the rear zone of the cervical canal or the front zone 4a of the uterine cavity 4 without the extension of the tip 34 from the support sleeve 102, the sperm is discharged from the straw 38 by the pushing of the piston rod 40. Depending on the morphology of the genital organ, after the tip extends from the support sleeve 102, the sperm can be ejected from the straw 38.

Although the invention has been shown and described with respect to the preferred embodiments, it will be understood by those skilled in the art that certain changes and modifications may be made without departing from the spirit and scope of the invention as defined in the following claims.

What is claimed is:

1. An artificial insemination and embryo transfer device, which comprises:

an elongate hollow tube;

a tip secured to a proximal end of said elongate tube, said tip having a conical front portion for smoothly passing it through a cervical canal of a female subject, a tapered middle portion integrally formed with the conical portion, a main body portion integrally formed with the middle portion, and a passage provided therein;

a piston rod slidably mounted in said elongate tube in an axial direction;

means retained between said elongate tube and said piston rod for restraining a free axial movement of the piston rod within said elongate tube;

first contamination preventing means enclosing said elongate tube for protecting said elongate tube against contamination from infectious materials in the cervical canal during the passing of the device through the cervical canal, said first contamination preventing means including a hollow cylindrical sheet wrapping around said elongate tube and in contact with said tip at a front end of the cylindrical sheet, the outer diameter of said cylindrical sheet being smaller than the largest diameter of said tip; and second contamination preventing means surrounding said tip and said cylindrical sheet for protecting them against contamination from infectious materials in a vaginal canal during the insertion of the device into the vaginal canal.

2. The device of claim 1, wherein said front end of said cylindrical sheet is thermally welded to an outer periphery of said tip, whereby said tip is threadedly engaged with the proximal end of said elongate tube by way of rotating said cylindrical sheet.

3. The device of claim 2, further comprising a cylindrical holder secured to a distal end of said elongate tube, wherein said cylindrical holder has a ring-shaped gripper movably carried thereon, and an annular projection formed at its end for preventing the gripper from escaping therefrom.

4. The device of claim 2 or 3, wherein said second contamination preventing means includes a tubular member wrapping around said tip and said cylindrical sheet and a rupturable thin film cap attached to a proximal end of said tubular member for covering the tip, whereby the film cap is ruptured by an advancement of the tip.

5. The device of claim 4, wherein said thin film cap has a plurality of radial tearing lines provided therein.

6. The device of claim 5, wherein said second contamination preventing means further includes a stretchable thin capsule secured to the proximal end of the tubular member and disposed inside the thin film cap for enwrapping the tip, said thin capsule having a breakable portion integrally formed therewith and arranged in a substantially coaxial relationship with the passage of the tip.

7. The device of claim 6, wherein said thin capsule has an annular projecting ring formed at its end, which is rigidly fixed to a stepped shoulder of the proximal end of the tubular member.

8. The device of claim 1, wherein said means for restraining the piston rod includes an O-ring held in an annular groove of the piston rod.

9. An artificial insemination and embryo transfer device, which comprises:

an elongate hollow tube having a flange provided at a distal end of the elongate tube;

a flexible tip secured to a proximal end of said elongate tube, said tip having a conical front portion for smoothly passing it through a cervical canal of a female subject, a tapered middle portion integrally formed with the conical portion, a main body portion extending from the middle portion in a length sufficient to enable the conical portion of the tip to reach a rearmost zone of a uterine horn of the subject female in the implantation of embryo, and a passage provided therein;

a piston rod slidably mounted in said elongate tube in an axial direction;

means retained between said elongate tube and said piston rod for restraining a free axial movement of the piston rod within said elongate tube;

a support sleeve housing said elongate tube and said main body portion of said tip and in contact with the tapered middle portion at its front end for supporting the tip so as to permit the deformation of the tip, said support sleeve having a flange provided at its rear end, the outer diameter of said support sleeve being smaller than the largest diameter of said tip;

first contamination preventing means enclosing said support sleeve and said tip for protecting them against contamination from infectious materials in the cervical canal during the passing of the device through the cervical canal; and second contamination preventing means surrounding said first contamination preventing means for protecting said first contamination preventing means against contamination from infectious materials in a vaginal canal during the insertion of the device into the vaginal canal.

10. The device of claim 9, wherein said main body of said tip is threadedly coupled with the proximal end of said elongate tube at its end.

11. The device of claim 9, further comprising an adapter interconnected between said elongate tube and said main body of said tip, said adapter threadedly engaged with the proximal end of said elongate tube, said adapter having a through hole in communication with the passage of the tip.

12. The device of claim 11, wherein said first contamination preventing means includes a flexible tube suitable for enclosing said tip and said support sleeve, said flexible tube being folded at its end so as to close an opening thereof.

13. The device of claim 12, wherein said second contamination preventing means includes a tubular member surrounding said flexible tube and having a rectangular flange provided at its distal end, and a rupturable thin film cap attached to a proximal end of said tubular member for covering the tip, whereby the film cap is ruptured by an advancement of the tip.

14. The device of claim 13, wherein said thin film cap has a plurality of radial tearing lines provided therein.

15. The device of claim 13, further comprising means provided at the flange of said support sleeve for holding the flange of said elongate tube and the rectangular flange of said tubular member.

16. The device of claim 15, wherein said holding means includes a mounting plate movable inserted around said flexible tube and disposed between the rectangular flange of said tubular member and the flange of said support sleeve, and a sliding bar engaged with a hole of the flange of said support sleeve and an aperture of said mounting plate and having grip rings carried by its ends.

17. The device of claim 16, wherein said sliding bar is made of a telescopic structure.

18. The device of claim 9, wherein said main body of said tip has at least one reinforcing wire embedded therein so as to adjust the flexibility thereof.

19. The device of claim 9, wherein said means for restraining the piston rod includes an O-ring held in an annular groove of the piston rod.

20. The device of claim 9, wherein said means for restraining the piston rod includes an annular spring-like element formed at the distal end of the elongate tube for exerting a pressure on the piston rod.

21. An artificial insemination and embryo transfer device, which comprises:

an elongate hollow tube having a flange provided at a distal end of the elongate tube;

a flexible tip secured to a proximal end of said elongate tube, said tip having a conical front portion for smoothly passing it through a cervical canal of a female subject, a tapered middle portion integrally formed with the conical portion, a main body portion extending from the middle portion in a length sufficient to enable the conical portion of the tip to reach a rearmost zone of a uterine horn of the subject female in the implantation of embryo, and a passage provided therein;

a piston rod slidably mounted in said elongate tube in an axial direction;

means retained between said elongate tube and said piston rod for restraining a free axial movement of the piston rod within said elongate tube;

a support sleeve housing said elongate tube and said main body portion of said tip and in contact with the tapered middle portion at its front end for supporting the tip so as to permit the deformation of the tip, said support sleeve having a flange provided at its rear end, the outer diameter of said support sleeve being smaller than the largest diameter of said tip;

contamination preventing means enclosing support sleeve and said tip for protecting them against contamination from infectious materials in a vaginal canal and the cervical canal during the introduction of the device into a uterine cavity, said contamination preventing means including a tubular member wrapping around said tip and said support sleeve and having a rectangular flange provided at a distal end of the tubular member, a rupturable thin film cap attached to a proximal end of the tubular member, and stretchable thin capsule secured to the proximal end of the tubular member and disposed inside the film cap for enwrapping the tip, said thin capsule having a breakable portion integrally formed therewith and arranged in a substantially coaxial relationship with the passage of the tip; and means provided at the flange of said support sleeve for holding the flange of said elongate tube and the rectangular flange of said tubular member.

22. The device of claim 21, wherein said main body of said tip has at least one reinforcing wire embedded therein so as to adjust the flexibility thereof.

23. The device of claim 21, further comprising an adapter interconnected between said elongate tube and said main body of said tip, said adapter threadedly engaged with the proximal end of said elongate tube, said adapter having a through hole in communication with the passage of the tip.

24. The device of claim 23, wherein said adapter includes a capillary tube fitted into the passage of said tip.

25. The device of claim 23, wherein said thin film cap has a plurality of radial tearing lines provided therein.

26. The device of claim 21, wherein said means for restraining the piston rod includes an O-ring held in an annular groove of the piston rod.

27. The device of claim 21, wherein said means for restraining the piston rod includes an annular spring-like element formed at the distal end of the elongate tube for exerting a pressure on the piston rod.

28. The device of claim 26 or 27, wherein said holding means includes a mounting plate movably inserted around said support sleeve and disposed between the rectangular flange of said tubular member and the flange of said support sleeve, and a sliding bar engaged with a hole of the flange of said support sleeve and an aperture of said mounting plate and having grip rings carried by its ends.

29. The device of claim 28, wherein said sliding bar is made of a telescopic structure.

30. The device of claim 21, wherein said support sleeve includes two detachable parts assembled together.

\* \* \* \* \*

UNITED STATES PATENT AND TRADEMARK OFFICE
CERTIFICATE OF CORRECTION

PATENT NO. : 5,496,272
DATED : March 5, 1996
INVENTOR(S) : CHUNG et al.

It is certified that error appears in the above-indentified patent and that said Letters Patent is hereby corrected as shown below:

Claim 4, col. 15, line 60, "claim 2 or 3" should read --claim 1, 2 or 3--.

Col. 15,
Claim 4, line 3, "sheet" should read --sheet,--.

Claim 16, col. 17, line 10, "movable" should read --movably--.

Signed and Sealed this

Twenty-first Day of May, 1996

Attest:

BRUCE LEHMAN

Attesting Officer    Commissioner of Patents and Trademarks